(12) United States Patent
Wickline et al.

(10) Patent No.: US 9,095,521 B2
(45) Date of Patent: Aug. 4, 2015

(54) METHODS FOR IMPROVING MUSCLE STRENGTH

(71) Applicant: The Washington University, St. Louis, MO (US)

(72) Inventors: Samuel A. Wickline, St. Louis, MO (US); Gregory M. Lanza, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 14/376,145

(22) PCT Filed: Feb. 1, 2013

(86) PCT No.: PCT/US2013/024397
§ 371 (c)(1),
(2) Date: Aug. 1, 2014

(87) PCT Pub. No.: WO2013/116691
PCT Pub. Date: Aug. 8, 2013

(65) Prior Publication Data
US 2015/0011578 A1    Jan. 8, 2015

Related U.S. Application Data

(60) Provisional application No. 61/594,182, filed on Feb. 2, 2012.

(51) Int. Cl.
*A61K 9/51* (2006.01)
*A61K 31/436* (2006.01)
*A61K 9/00* (2006.01)

(52) U.S. Cl.
CPC .......... *A61K 9/51* (2013.01); *A61K 9/0019* (2013.01); *A61K 9/5115* (2013.01); *A61K 9/5123* (2013.01); *A61K 31/436* (2013.01)

(58) Field of Classification Search
CPC ............................... A61K 9/51; A61K 31/436
See application file for complete search history.

(56) References Cited

U.S. PATENT DOCUMENTS

| | | | |
|---|---|---|---|
| 4,927,623 A | 5/1990 | Long, Jr. | |
| 5,077,036 A | 12/1991 | Long, Jr. | |
| 5,114,703 A | 5/1992 | Wolf et al. | |
| 5,171,755 A | 12/1992 | Kaufman et al. | |
| 5,304,325 A | 4/1994 | Kaufman et al. | |
| 5,350,571 A | 9/1994 | Kaufman et al. | |
| 5,393,524 A | 2/1995 | Quay | |
| 5,403,575 A | 4/1995 | Kaufman et al. | |
| 5,690,907 A | 11/1997 | Lanza et al. | |
| 5,780,010 A | 7/1998 | Lanza et al. | |
| 5,958,371 A | 9/1999 | Lanza et al. | |
| 5,989,520 A | 11/1999 | Lanza et al. | |
| 2007/0225315 A1 | 9/2007 | Guttridge et al. | |

FOREIGN PATENT DOCUMENTS

| EP | 1829530 A2 | 9/2007 |
|---|---|---|
| WO | 2009/049242 A1 | 4/2009 |

OTHER PUBLICATIONS

Hoffman et al., "Dystrophin: The Protein Product of the Duchenne Muscular Dystrophy Locus", Cell, 1987, pp. 919-928, vol. 51, No. 6.
Hu et al., "Imaging of Vx-2 rabbit tumors with αvβ3-integrin-targeted 111 in nanoparticles", Int. J. Cancer, 2007, pp. 1951-1957, vol. 120, No. 9.
International Search Report and Written Opinion from related International Application No. PCT/US2013/024397, dated Feb. 1, 2013, 6 pgs.
Iyer et al., "Exploiting the enhanced permeability and retention effect for tumor targeting", Drug Discovery Today, 2006, pp. 812-818, vol. 11, No. 17-18.
Ju et al., "Valosin-containing protein (VCP) is required for autophagy and is disrupted in VCP disease", J. Cell Biol., 2009, pp. 875-888, vol. 187, No. 6.
Ju et al., "Quantitation of "autophagic flux" in mature skeletal muscle", Autophagy, 2010, pp. 929-935, vol. 6, No. 7.
Katre et al. "Multivesicular Liposome (DepoFoam) Technology for the Sustained Delivery of Insulin-like Growth Factor-I (IGF-I)", Journal of Pharmaceutical Sciences, 1998, pp. 1341-1346, vol. 87, No. 11.
Keeling et al., "Weekly Oral Prednisolone Improves Survival and Strength in Male mdx Mice", Muscle & Nerve, 2007, pp. 43-48, vol. 35, No. 1.
Kilarski et al., "Systematic distribution of muscle fibre types in the rat and rabbit diaphragm: a morphometric and ultrastructural analysis", J. Anat., 1990, pp. 13-30, vol. 168.
Levine et al., "Autophagy in the Pathogenesis of Disease", Cell, 2008, pp. 27-42, vol. 132, No. 1.
Maeda et al., "Polymeric drugs for efficient tumor-targeted drug delivery based on EPR-effect", European Journal of Pharmaceutics and Biopharmaceutics, 2009, pp. 409-419, vol. 71, No. 3.
Mammucari et al., "FoxO3 Controls Autophagy in Skeletal Muscle In Vivo", Cell Metabolism, 2007, pp. 458-471, vol. 6, No. 6.
Markham et al., "Steroid Therapy and Cardiac Function in Duchenne Muscular Dystrophy", Pediatric Cardiology, 2005, pp. 768-771, vol. 26, No. 6.
McGeachie et al., "Age-related changes in replication of myogenic cells in mdx mice: quantitative autoradiographic studies", Journal of the Neurological Sciences, 1993, pp. 169-179, vol. 119, No. 2.
Mouisel et al., "Muscle Weakness and Atrophy Are Associated with Decreased Regenerative Capacity and Changes in mTOR Signaling in Skeletal Muscles of Venerable (18-24-month-old) Dystrophic mdx Mice", Muscle & Nerve, 2010, pp. 809-818, vol. 41, No. 6.
Mourkioti et al., "Targeted ablation of IKK2 improves skeletal muscle strength, maintains mass, and promotes regeneration", The Journal of Clinical Investigation, 2006, pp. 2945-2954, vol. 116, No. 11.
Moxley et al., "Practice Parameter: Corticosteroid treatment of Duchenne dystrophy: Report of the Quality Standards Subcommittee of the American Academy of Neurology and the Practice Committee of the Child Neurology Society", Neurology, 2005, pp. 13-20, vol. 64, No. 1.

(Continued)

*Primary Examiner* — Bruck Kifle
(74) *Attorney, Agent, or Firm* — Polsinelli PC

(57) ABSTRACT

The present invention relates to methods for improving muscle strength and treating muscular dystrophy.

20 Claims, 10 Drawing Sheets

(56) References Cited

OTHER PUBLICATIONS

Napoli et al., "Distribution of Sirolimus in Rat Tissue", Clinical Biochemistry, 1997, pp. 135-142, vol. 30, No. 2.

Nelson et al., "Emerging genetic therapies to treat Duchenne muscular dystrophy", Curr. Opin. Neurol., 2009, pp. 532-538, vol. 22, No. 5.

Ogata et al., "Beneficial effects of beta-blockers and angiotensin-converting enzyme inhibitors in Duchenne muscular dystrophy", Journal of Cardiology, 2009, pp. 72-78, vol. 53, No. 1.

O'Reilly et al., "Comparative pharmacokinetics of RAD001 (everolimus) in normal and tumor-bearing rodents", Cancer Chemother. Pharmacol., 2010, pp. 625-639, vol. 65, No. 4.

Pan et al., "Nanomedicine: Perspective and promises with ligand-directed molecular imaging", European Journal of Radiology, 2009, pp. 274-285, vol. 70, No. 2.

Raben et al., "Suppression of autophagy in skeletal muscle uncovers the accumulation of ubiquitinated proteins and their potential role in muscle damage in Pompe disease", Human Molecular Genetics, 2008, pp. 3897-3908, vol. 17, No. 24.

Rafael-Fortney et al., "Early Treatment With Lisinopril and Spironolactone Preserves Cardiac and Skeletal Muscle in Duchenne Muscular Dystrophy Mice", Circulation, 2011, pp. 582-588, vol. 124, No. 5.

Risson et al., "Muscle inactivation of mTOR causes metabolic and dystrophin defects leading to severe myopathy", J. Cell Biol., 2009, pp. 859-874, vol. 187, No. 6.

Sandri, "Autophagy in health and disease. 3. Involvement of autophagy in muscle atrophy", Am. J. Physiol. Cell Physiol., 2010, pp. C1291-C1297, vol. 298, No. 6.

Schmieder et al., "Molecular MR Imaging of Melanoma Angiogenesis With $\alpha v\beta 3$-Targeted Paramagnetic Nanoparticles", Magnetic Resonance in Medicine, 2005, pp. 621-627, vol. 53, No. 3.

Shigemitsu et al., "Regulation of Translational Effectors by Amino Acid and Mammalian Target of Rapamycin Signaling Pathways. Possible Involvement of Autophagy in Cultured Hepatoma Cells", The Journal of Biological Chemistry, 1999, pp. 1058-1065, vol. 274, No. 2.

Stepkowski, "Preclinical Results of Sirolimus Treatment in Transplant Models", Transplantation Proceedings, 2003, pp. 219S-226S, vol. 35 (Suppl 3A).

Thomson et al., "Immunoregulatory Functions of mTOR Inhibition", Nat. Rev. Immunol., 2009, pp. 324-337, vol. 9, No. 5.

Vilquin et al., "Successful Myoblast Allotransplantation in mdx Mice Using Rapamycin", Transplantation, 1995, pp. 422-439, vol. 59, No. 3.

Williams et al., "Resting Calcium Concentrations in Isolated Skeletal Muscle Fibres of Dystrophic Mice", Journal of Physiology, 1990, pp. 243-256, vol. 428.

Winter et al., "Endothelial $\alpha v\beta 3$ Integrin-Targeted Fumagillin Nanoparticles Inhibit Angiogenesis in Atherosclerosis", Arterioscler. Thromb. Vasc. Biol., 2006, pp. 2103-2109, vol. 26, No. 9.

Wullschleger et al., "TOR Signaling in Growth and Metabolism", Cell, 2006, pp. 471-484, vol. 124, No. 3.

Ye et al., "DepoFoam technology: a vehicle for controlled delivery of protein and peptide drugs", Journal of Controlled Release, 2000, pp. 155-166, vol. 64.

Zeman et al., "Regulation of Protein Degradation in Muscle by Calcium. Evidence for Enhanced Nonlysosomal Proteolysis Associated With Elevated Cytosolic Calcium", The Journal of Biological Chemistry, 1985, pp. 13619-13624, vol. 260, No. 25.

Zeman et al., "Regulation of Ca2+-dependent protein turnover in skeletal muscle by thyroxine", Biochem. J., 1986, pp. 269-272, vol. 240.

Adelman, "Sirolimus and its Analogs and its Effects on Vascular Diseases", Current Pharmaceutical Design, 2010, pp. 4002-4011, vol. 16, No. 36.

Ahern et al., "Ryanodine receptors from rabbit skeletal muscle are reversibly activated by rapamycin", Neuroscience Letters, 1997, pp. 81-84, vol. 225, No. 2.

Avila et al., "FKBP12 Binding to RyR1 Modulates Excitation-Contraction Coupling in Mouse Skeletal Myotubes", The Journal of Biological Chemistry, 2003, pp. 22600-22608, vol. 278, No. 25.

Avila et al., "Rapamycin and FK506 reduce skeletal muscle voltage sensor expression and function", Cell Calcium, 2005, pp. 35-44, vol. 38, No. 1.

Balaban et al., "Corticosteroid Treatment and Functional Improvement in Duchenne Muscular Dystrophy: Long-Term Effect", Am. J. Phys. Med. Rehabil., 2005, pp. 843-850, vol. 84, No. 11.

Bellinger et al., "Hypernitrosylated ryanodine receptor/calcium release channels are leaky in dystrophic muscle", Nat. Med., 2009, pp. 325-350, vol. 15, No. 3.

Bentzinger et al., "Skeletal Muscle-Specific Ablation of raptor, but Not of rictor, Causes Metabolic Changes and Results in Muscle Dystrophy", Cell Metabolism, 2008, pp. 411-424, vol. 8, No. 5.

Biggar et al., "Long-term benefits of deflazacort treatment for boys with Duchenne muscular dystrophy in their second decade", Neuromuscular Disorders, 2006, pp. 249-255, vol. 16, No. 4.

Blanco et al., "Nanomedicine in cancer therapy: Innovative trends and prospects", Cancer Science, 2011, pp. 1247-1252, vol. 102, No. 7.

Bodensteiner et al., "Intracellular calcium accumulation in Duchenne dystrophy and other myopathies: A study of 567,000 muscle fibers in 114 biopsies", Neurology, 1978, pp. 439-446, vol. 28, No. 5.

Bulfield et al., "X chromosome-linked muscular dystrophy (mdx) in the mouse", Proc. Natl. Acad. Sci. USA, 1984, pp. 1189-1192, vol. 81, No. 4.

Chamberlain et al. "Treatment of Leptomeningeal Metastasis With Intraventricular Administration of Depot Cytarabine (DTC 101)", Arch. Neurol., 1993, pp. 261-264, vol. 50.

Crowe et al., "Absorption and Intestinal Metabolism of SDZ-RAD and Rapamycin in Rats", Drug Metabolism and Disposition, 1999, pp. 627-632, vol. 27, No. 5.

Cunningham et al., "mTOR controls mitochondrial oxidative function through a YY1-PGC-1$\alpha$ transcriptional complex", Nature, 2007, pp. 736-740, vol. 450, No. 7170.

Cyrus et al., "Intramural Delivery of Rapamycin With $\alpha v\beta 3$-Targeted Paramagnetic Nanoparticles Inhibits Stenosis After Balloon Injury", Arterioscler. Thromb. Vasc. Biol., 2008, pp. 820-826, vol. 28, No. 5.

Eghtesad et al., "Rapamycin Ameliorates Dystrophic Phenotype in mdx Mouse Skeletal Muscle", Mol. Med., 2011, pp. 917-924, vol. 17, No. 9-10.

Gonzalez et al., "The emerging role of autophagy in the pathophysiology of diabetes mellitus", Autophagy, 2011, pp. 2-11, vol. 7, No. 1.

Greish, "Enhanced permeability and retention of macromolecular drugs in solid tumors: A royal gate for targeted anticancer nanomedicines", Journal of Drug Targeting, 2007, pp. 457-464, vol. 15, No. 7-8.

Grumati et al., "Autophagy is defective in collagen VI muscular dystrophies, and its reactivation rescues myofiber degeneration", Nature Medicine, 2010, pp. 1313-1320, vol. 16, No. 11.

H&E

Nanoparticle
(Rhodamine)

Rapamycin
(Cy7)

METHODS FOR IMPROVING MUSCLE STRENGTH

STATEMENT OF GOVERNMENTAL RIGHTS

The invention was made with governmental support under R01 AR056223 awarded by the National Institutes of Health. The government has certain rights in the invention.

FIELD OF THE INVENTION

The invention relates to methods for improving muscle strength and treating muscular dystrophy.

BACKGROUND OF INVENTION

Neuromuscular diseases such as muscular dystrophy (MD) and aging weaken the musculoskeletal system and hamper locomotion. Both conditions may be characterized by progressive skeletal muscle weakness, defects in muscle proteins, and the death of muscle cells and tissue. Physical therapy, occupational therapy, orthotic intervention, orthopedic instruments, speech therapy, aerobic exercise, low intensity anabolic steroids, and anti-inflammatory steroid supplements may be helpful, but do not reverse or generate long lasting improvements in muscle strength without consequential side effects. A continuing need exists, therefore, for alternative methods to improve skeletal, diaphragmatic, and cardiac muscle strength in aging subjects, and subjects with neuromuscular diseases such as muscular dystrophy, either as a primary therapy or as an adjunctive steroid-sparing combination therapeutic.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE PREFERRED EMBODIMENTS

Figure 1:
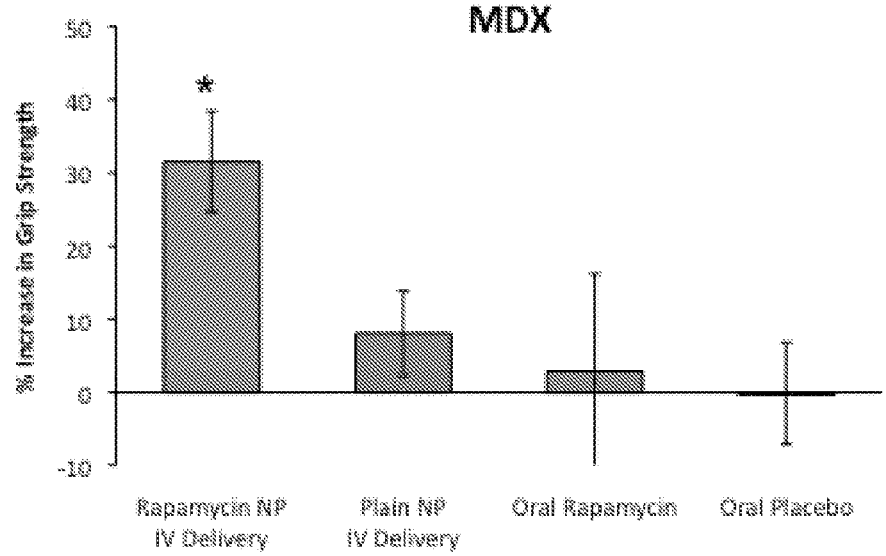
FIG. 1 graphically depicts improved strength in mdx mice treated with rapamycin-loaded nanoparticle. (A) Four weeks of treatment with rapamycin-loaded nanoparticles delivered intravenously significantly increased weight-normalized grip strength in 14-week old mdx animals vs. groups given plain nanoparticles IV, equivalent oral doses of rapamycin, or oral placebo (p<0.012, p<0.027, and p<0.016, respectively, using Fisher's protected least significant difference at 5% significance level). (B) No significant difference in strength was observed for age-matched wild-type mice given either plain or rapamycin-loaded nanoparticles intravenously or oral rapamycin. (C) The increase in weight-normalized strength in a subset of mdx mice treated with IV rapamycin nanoparticles occurred in both young (14-18 wk) and old (34-38 wk) animals (p=0.008 using a linear contrast model comparing pre- to post-treatment differences). Absolute values of the mean change in strength between time points are shown in columns with standard error bars. (D) Wild-type mice given similar treatment and drug-holiday exhibit no significant difference between pre- and post-treatment strength (p=0.598).
Figure 1:
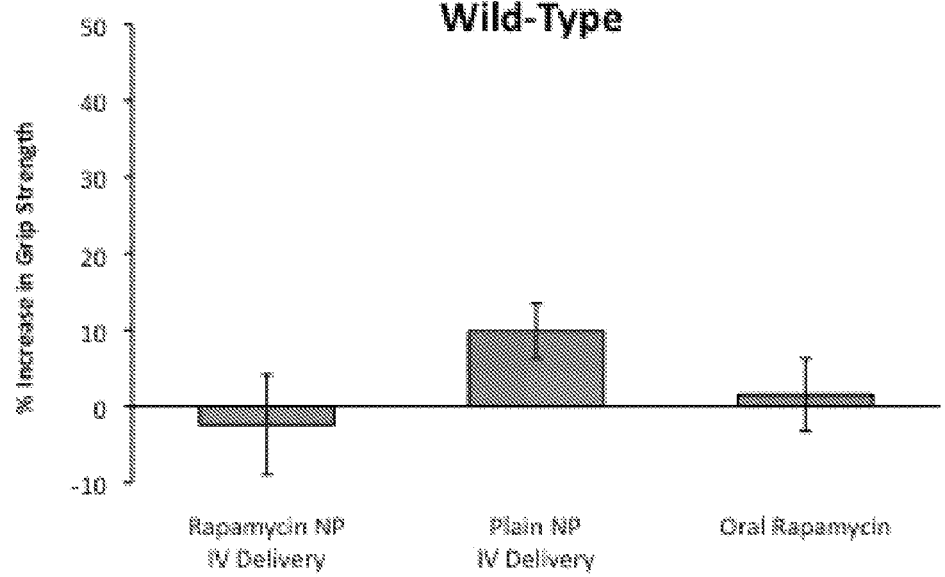
Figure 1:
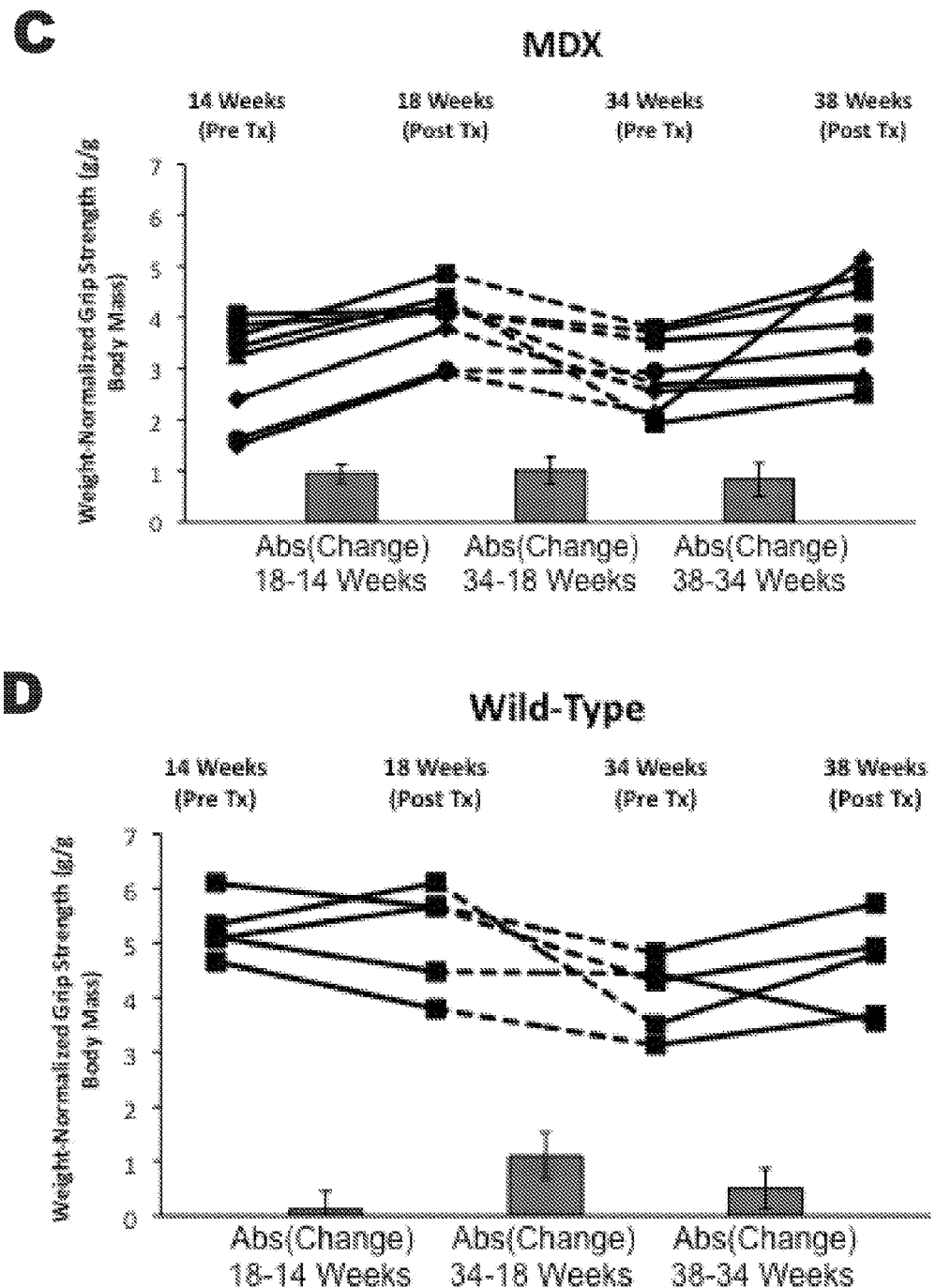

A method for increasing muscle strength in a subject has been developed. According to the invention, it has been discovered that administration of rapamycin-loaded nanoparticles (RNP) significantly increases muscle strength in a model of muscular dystrophy (MD) and in aging subjects. Notably, these effects are not seen with oral rapamycin alone in dosing concentrations and amounts that are typical of clinical usage. The inventors also discovered that administering RNPs may increase muscle strength by inducing autophagy in multiple muscle groups that are affected heterogeneously by MD or aging.

(a) Subject

The inventors discovered that administration of rapamycin-loaded nanoparticles (RNPs) increases muscle strength in a subject. In some embodiments, the subject may be an animal. Non-limiting examples of an animal in which muscle strength may be increased include a rodent, a human, a livestock animal, a companion animal, a laboratory animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In another embodiment, the subject may be a zoological animal. As used herein, a "zoological animal" refers to an animal that may be found in a zoo. Such animals may include non-human primates, large cats, wolves, and bears.

In some embodiments, the subject is a human. Typically, a human subject may be a healthy human subject, or may be suffering from muscle weakness. For instance, a subject of the invention may be suffering from muscle weakness resulting from aging, a traumatic injury or surgery, or may have a neuromuscular disorder that may produce muscle weakness.

In one embodiment, the human subject may be healthy. In another embodiment, the subject may be suffering from muscle weakness resulting from a traumatic injury or surgery. As used herein, "trauma" is a body wound or shock produced by sudden physical injury as from violence or accident or a physical wound or injury, such as a fracture, blow, or surgical procedure, which results in major muscle tissue damage.

In yet another embodiment, the subject may be suffering from muscle weakness resulting from aging. An aging human subject may be at least about 40, 45, 50, 55, 60, 65, 70, 75, 80, 85, 90, 95 years of age or older.

In another embodiment, the subject may be suffering from heart failure. For instance, a subject may be suffering from heart failure due to coronary artery disease; atherosclerosis; hypertrophic cardiomyopathy such as idiopathic or non-obstructive hypertrophic cardiomyopathy; congenital, hypertensive, or infectious heart disease; heart failure induced by toxic substances such as drugs, heavy metals, radiation; or due to diastolic heart failure.

In still another embodiment, the human subject may have a neuromuscular disorder that may produce muscle weakness. As used herein, "neuromuscular disorder" refers to a disorder that affects the peripheral nervous system. The peripheral nervous system includes muscles, the nerve-muscle (neuromuscular) junction, peripheral nerves in the limbs, and the motor-nerve cells in the spinal cord. Non-limiting examples of neuromuscular disorders may include polymyalgia rheumatica (muscle rheumatism), polymyositis, dermatomyositis, bramaticosis and inclusion body myositis, rhabdomyolysis, amyotrophic lateral sclerosis, asarcoglycanopathy, multiple sclerosis, myasthenia gravis, muscular dystrophy, spinal and bulbar muscular atrophy of Kennedy, late-onset Finkel type spinal muscular atrophy, spinal muscular atrophy-1, spinal muscular atrophy-2, spinal muscular atrophy-3, spinal muscular atrophy-4, spinal muscular atrophy, distal, type V, spinal muscular atrophy, distal, type V, spinal muscular atrophy juvenile, and spinal muscular atrophy with respiratory distress.

In some embodiments, the subject has muscular dystrophy. As used herein, "muscular dystrophy" refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 2I muscular dystrophy, limb-girdle type 2I muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In an exemplary embodiment, the subject has Duchenne muscular dystrophy.

Methods of diagnosing a subject with muscle weakness, muscular dystrophy, heart failure, and the like are known in the art.

In some embodiments, the subject may be a lab animal. Non-limiting examples of a lab animal may include a rabbit, a mouse, a guinea pig, a hamster, or a rat. In one embodiment, the subject may be a lab animal. In preferred embodiments, the lab animal may be a model animal for a neuromuscular disease. Non-limiting examples of lab animals that may be used as models for neuromuscular disease may include the mdx mouse Duschenne muscular dystrophy (DMD) model, the canine golden retriever muscular dystrophy (MD) model, the SJL/J mouse autosomal recessive limb-girdle MD model, the BIO14.6 hamster sarcoglycanopathies (SG) model and other sarcoglycan null mutant animal models, the dy/dy (dystrophia-muscularis) mouse and the dy2J/dy2J mouse models for congenital MD, the myodystrophy mouse (Largemyd) model, and pig comprising mutations in the porcine Ryr1 gene as a model for malignant hyperthermia and Central Core myopathy.

In some embodiments, RNP may be administered to a culture of muscle cells. Non-limiting examples of cultured muscle cells may include a myoblast cell line that give rise to muscle cells, or differentiated muscle cells or myocytes. The muscle cells may be, or the myoblasts may give rise to skeletal muscle, smooth muscle, or cardiac muscle. In some embodiments, RNP may be administered to ex vivo muscle cells derived from a subject.

(b) Muscle Strength

In some embodiments, the method comprises administering RNPs to a subject to increase muscle strength. According to the invention, muscle strength may be increased by RNP interaction with the mTORC1 pathway. The inventors discovered that RNP interaction with the mTORC1 pathway may increase muscle strength by inducing autophagy and attenuating muscle destruction or reducing inflammation. In some embodiments, muscle strength may be increased by attenuating muscle destruction or reducing inflammation. In other embodiments, muscle strength may be increased by inducing autophagy.

In other embodiments, the method comprises administering RNPs to increase muscle strength in a subject suffering from muscle weakness resulting from a traumatic injury or surgery. In one embodiment, administering RNPs to a subject suffering from muscle weakness resulting from a traumatic injury or surgery increases muscle strength by inducing autophagy. In another embodiment, administering RNPs to a subject suffering from muscle weakness resulting from a traumatic injury or surgery increases muscle strength by attenuating muscle destruction. In yet another embodiment, administering RNPs to a subject suffering from muscle weakness resulting from a traumatic injury or surgery increases muscle strength by reducing inflammation.

In yet other embodiments, the method comprises administering RNPs to a subject suffering from muscle weakness resulting from aging to increase muscle strength. In one embodiment, administering RNPs to a subject suffering from muscle weakness resulting from aging increases muscle strength by inducing autophagy. In another embodiment, administering RNPs to a subject suffering from muscle weakness resulting from aging increases muscle strength by attenuating muscle destruction. In another embodiment, administering RNPs to a subject suffering from muscle weakness resulting from aging increases muscle strength by reducing inflammation.

In other embodiments, the method comprises administering RNPs to a subject with muscular dystrophy to increase muscle strength. In one embodiment, administering RNPs to a subject with muscular dystrophy increases muscle strength by inducing autophagy. In another embodiment, administering RNPs to a subject with muscular dystrophy increases muscle strength by attenuating muscle destruction. In yet another embodiment, administering RNPs to a subject with muscular dystrophy increases muscle strength by reducing inflammation.

In some embodiments, administering RNPs induces autophagy in muscle cells. In another embodiment, administering RNPs attenuates muscle destruction. In yet another embodiment, administering RNPs reduces inflammation.

Methods of measuring muscle strength are known in the art. In general, methods of measuring muscle strength and function vary depending on the muscle groups to be measured, and the animal whose muscle strength is being measured. In humans for instance, abdominal muscle strength may be measured using a sit-up test, the chair stand may be used to measure lower body muscle strength and function, the arm curl test may be used to measure upper body muscle strength, and leg strength may be measured using the maximum voluntary contraction (MVC), which measures the peak force produced by a muscle as it contracts while pulling against an immovable object. Diaphragm strength may be measured by standard pulmonary function tests. Cardiac strength may be measured by echocardiography, invasive right and left heart cardiac catheterization, CT, MRI, PET, or other imaging tests known to clinicians. In animal models such as the mouse, muscle strength may be measured using forelimb grip strength, treadmill exercise time over some interval of time, swimming time, or other like physical measure. Other suitable means of measuring muscle strength are known in the art. Similarly, methods of measuring autophagy are known in the art.

In some embodiments, muscle strength may be improved by about 1, 2, 3, 4, 5, 6, 7, 8, 9, 10, 15, 16, 17, 18, 19, 20, 21, 22, 23, 24, 25, 26, 27, 28, 29, or 30% or more after a subject is administered RNP compared to before the subject is administered RNP. In other embodiments, muscle strength may be improved by about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% or more after a subject is administered RNP compared to before the subject is administered RNP. In yet other embodiments, muscle strength may be improved by about 10, 15, 20, 25, 30, 35, 40, 45, 50, 55, 60, 65% or more after a subject is administered RNP compared to before the subject is administered RNP. In an exemplary alternative of the embodiments, muscle strength may be improved about 7-9% after a subject is administered RNP compared to before the subject is administered RNP. In another exemplary alternative of the embodiments, muscle strength may be improved about 13-15% after a subject is administered RNP compared to before the subject is administered RNP. In yet another exemplary alternative of the embodiments, muscle strength may be improved about 25-30% after a subject is administered RNP compared to before the subject is administered RNP.

(c) Nanoparticles

The method of the invention comprises administering rapamycin-loaded nanoparticles (RNP). As used herein, "nanoparticle" is used to refer to a nanostructure that is typically between about 5 nM and 400 nM across the largest dimension of the structure. A nanoparticle of the invention may be spherical, but is not required to be spherical. Regardless of the shape of the nanoparticle, the nanoparticle should be capable of comprising rapamycin.

Non-limiting examples of suitable nanoparticles may include liposomes, poloxamers, microemulsions, micelles, dendrimers and other phospholipid-containing systems, and perfluorocarbon nanoparticles.

In one embodiment, a liposome delivery vehicle may be utilized. Liposomes, depending upon the embodiment, are suitable for delivery of rapamycin in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells.

Liposomes may be comprised of a variety of different types of phosholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tetradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl,oleoyl PS, palmitoyl,linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N -trimethyl ammonium chloride, 1,1'-dioctadecyl-3,3,3',3'-tetramethylindocarbocyanine, 3,3'-deheptyloxacarbocyanine iodide, 1,1'-dedodecyl-3,3,3',3'-tetramethylindocarbocyanine perchloarate, 1,1'-dioleyl-3,3, 3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying the composition of the invention may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, the composition of the invention may be delivered to a tissue or cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear, but also may appear as a milky colloidal suspension depending on exact composition, storage conditions, pH, temperature, surface charge, shape, and such. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions may optimally comprise phospholipids, although other hydrophobic core components singularly or in mixtures (e.g., perfluorocarbons: see below) may contribute to the composition of the particle. Any of the phospholipids detailed above for liposomes are suitable for embodiments directed to microemulsions. The composition of the invention may be encapsulated in a microemulsion by any method generally known in the art.

In yet another embodiment, the composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate or conjugate rapamycin via standard linker chemistries known in the art. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

In preferred embodiments, a nanoparticle of the invention may be a perfluorocarbon nanoparticle. Such nanoparticles are known in the art. For instance, see U.S. Pat. Nos. 5,690, 907; 5,780,010; 5,989,520 and 5,958,371, each hereby incorporated by reference in their entirety.

Useful perfluorocarbon emulsions are disclosed in U.S. Pat. Nos. 4,927,623, 5,077,036, 5,114,703, 5,171,755, 5,304, 325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether. In some embodiments, the perfluorocarbon compound is perfluoro-n-octyl bromide. In other embodiments, the perfluorocarbon compound may be a perfluoroalkylated crown ether.

The coating which comprises lipid/surfactant to form an outer coating on the nanoparticles may include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids, including DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol,1,2-diacyl-3-trimethylammonium-propane; 1,2-diacyl-3-dimethylammonium -propane; 1,2-diacyl-sn-glycerol-3-ethyl phosphocholine; and 3.beta.-[N',N'-dimethylaminoethane)-carbamol]cholesterol-HCl, may also be used.

Perfluorocarbon nanoparticles are typically formed by microfluidizing a mixture of the fluorocarbon lipid which forms the core and the lipid/surfactant mixture which forms the outer layer in suspension in aqueous medium to form an emulsion. Sonication or other techniques may be required to obtain a suspension of the lipid/surfactant in the aqueous medium. The components of the outer layer may also be coupled to imaging agents or radionuclides.

In some embodiments, the RNPs may be targeted to muscle tissue. Methods of targeting nanoparticles are known in the art. For instance, targeted nanoparticles may comprise targeting molecules. Alternatively, the prominent inflammatory response and consequential increased vascular permeability, together with enhanced sarcolemmal membrane permeability observed in muscle tissue of subjects with neuromuscular disease might establish favorable conditions for effective targeting of the nanoparticle, in analogy to the mechanism of enhanced permeability and retention (EPR) utilized in cancer nanotherapeutics.

In some embodiments, the RNPs are targeted to muscle tissue using EPR. In other embodiments, the nanoparticle may further comprise targeting molecules, such that nanoparticles comprising targeting molecules may be delivered and concentrated at desired sites. Targeted nanoparticles may include a wide variety of targeting molecules, including but not limited to, antibodies, antibody fragments, peptides, small molecules, polysaccharides, nucleic acids, aptamers, peptidomimetics, other mimetics and drugs alone or in combination. These targeting molecules may be utilized to specifically bind the nanoparticles to cellular epitopes and receptors, and may be attached directly or indirectly to the nanoparticle.

Direct attachment of the targeting molecules to the nanoparticle refers to the preparation of a targeting molecule-nanoparticle complex wherein the targeting molecule is covalently bound to the nanoparticle. Alternatively, direct attachment also may refer to the preparation of a targeting molecule-nanoparticle complex wherein the targeting molecule is covalently bound to a linker, which is in turn bound to the nanoparticle.

Indirect attachment refers to forming a complex between the nanoparticle and the targeting molecule in vivo in two or more steps. Indirect attachment utilizes a chemical linking system to produce the close and specific apposition of the nanoparticle to a targeted cell or tissue surface. A non-limiting example of an indirect targeting system is avidin-biotin.

Avidin-biotin interactions are useful noncovalent targeting systems that have been incorporated into many biological and analytical systems and selected in vivo applications. Avidin has a high affinity for biotin (10-15 M) facilitating rapid and stable binding under physiological conditions. Targeted systems utilizing this approach are administered in two or three steps, depending on the formulation. Typically, a biotinylated ligand, such as a monoclonal antibody, is administered first and "pretargeted" to the unique molecular epitopes. Next, avidin is administered, which binds to the biotin moiety of the "pretargeted" ligand. Finally, the biotinylated nanoparticle is added and binds to the unoccupied biotin-binding sites remaining on the avidin thereby completing the biotinylated ligand-avidin-nanoparticle "sandwich". The avidin-biotin approach can avoid accelerated, premature clearance of targeted particles by the mononuclear phagocyte system (MPS) secondary to the presence of surface antibody. Additionally, avidin, with four independent biotin-binding sites provides signal amplification and improves detection sensitivity.

A targeting molecule may be directly attached to a nanoparticle by a variety of methods depending upon the nature of the targeting molecule and the nanoparticle. Direct chemical conjugation of targeting molecules to proteinaceous nanoparticles often take advantage of numerous amino-groups (e.g. lysine) inherently present within the nanoparticle. Alternatively, functionally active chemical groups such as maleimide or NHS groups may be incorporated into the nanoparticle as chemical "hooks" for targeting molecule conjugation after the nanoparticles are formed. Another common approach is to activate polymer carboxylates with carbodiimide prior to targeting molecule addition. Alternatively, cell membrane inserting peptide linkers may be used to attach the drug cargo to the nanoparticle in a postformulation step as described previously in U.S. patent application Ser. No. 12/910,385, the disclosure of which is hereby incorporated by reference in its entirety.

The selected covalent attachment strategy is primarily determined by the chemical nature of the targeting molecule. For instance, monoclonal antibodies and other large proteins may denature under harsh processing conditions whereas the bioactivity of carbohydrates, short peptides, aptamers, drugs or peptidomimetics often can be preserved under these conditions.

To ensure high targeting molecule binding integrity and maximize targeted particle avidity flexible linkers, e.g. polyethylene glycol, amino acids or simple caproate bridges, can be inserted between the nanoparticle and the targeting molecule. These linkers may be 2 nm or longer and may minimize interference of targeting molecule binding by nanoparticle surface interactions. Non-limiting examples of linkers may include carbodiimide linkers and N-hydroxysuccinimide esters. The linkers may be heterobifunctional or homobifunctional.

In some embodiments, the rapamycin or rapamycin analogue may be delivered to the muscle in a depot. As used herein, "depot" refers to any delivery mechanism known in the art to concentrate and release the rapamycin or a rapamycin analogue in the muscle tissue over time to provide a pharmaceutically effective amount. For instance, in some embodiments, injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. (see, for instance, Chamberlain et al. Arch. Neuro. 50: 261-264, 1993; Katri et al. J. Pharm. Sci. 87: 1341-1346, 1998; Ye et al., J. Control Release 64: 155-166, 2000; and Howell, Cancer J. 7: 219-227, 2001). In certain embodiments, a nanoparticle as described above serves as the depot.

(d) Rapamycin-loaded Nanoparticles

The method of the invention utilizes rapamycin-loaded nanoparticles. Rapamycin binds the cytosolic protein FK-binding protein 12 (FKBP12) and inhibits the mammalian target of rapamycin (mTOR) pathway by directly binding the mTOR Complex1 (mTORC1). As such, nanoparticles of the invention may be loaded with any compound capable of inhibiting the mTOR pathway. In some embodiments, the nanoparticles may be loaded with rapamycin or a rapamycin analog. Non-limiting examples of rapamycin analogs that may be used in the invention may include CCI-779 (Temsirolimus), C20-methallylrapamycin, C16-(S)-3-methylindolerapamycin, C16-iRap, AP21967 (C16-AiRap), and AP23573. In some embodiments, the nanoparticles may be loaded with CCI-779. In other embodiments, the nanoparticles may be loaded with C20-methallylrapamycin. In yet other embodiments, the nanoparticles may be loaded with C16-(S)-3-methylindolerapamycin. In still other embodiments, the nanoparticles may be loaded with C16-iRap. In further embodiments, the nanoparticles may be loaded with AP21967. In yet still other embodiments, the nanoparticles may be loaded with AP23573. In preferred embodiments, the nanoparticles may be loaded with rapamycin. In another preferred embodiment, the nanoparticles may be loaded with one or more inducers of autophagy. Non-limiting examples may include inhibitors of mTOR, such as tamoxifen, perhexiline, amiodaronel, niclosamide, rottlerin, torin1, PI103 and structurally related compounds, phenethyl isothiocyanate (PEITC), and dexamethasone, or mTOR independent inducers, such as lithium, carbamazepine, sodium valproate, verapamil, loperamide, amiodaronel, nimodipine, nitrendipine, niguldipine, nicardipine, pimozide, calpastatin, calpeptin, clonidine, rilmenidine, 2',5'-Dideoxyadenosine, NF449, minoxidil, penitrem A, trehalose, spermidine, resveratrol, fluspirilene, trifluoperazine, SMERs (SMER10, SMER18, SMER28 and analogs), and dorsomorphin. Other potentially suitable autophagy inducers may be known in the art.

Methods of incorporating compositions such as rapamycin into delivery vehicles are known in the art and described above. In exemplary embodiments, rapamycin may be incorporated into PFC nanoparticles as described in the Examples. In other embodiments, conjugation of rapamycin to lipid, peptide or other linkers that insert into the nanoparticle membrane may be used. In other embodiments, rapamycyin carried in the core of the particle (e.g., liposomes) may be used. The concentration of rapamycin in the nanoparticles can and will vary. In some embodiments, the RNP particles may comprise about 0.1, 0.2, 0.3, 0.4, 0.5, 0.6, 0.7, 0.8, 0.9 or about 1 mole % rapamycin or rapamycin analogue. In other embodiments, the RNP particles may comprise about 0.2, 0.21, 0.22, 0.23, 0.24, 0.25, 0.26, 0.27, 0.28, 0.29, or about 0.3 mole % rapamycin or rapamycin analogue. In yet other embodiments, the RNP particles may comprise about 0.271, 0.272, 0.273, or 0.274, 0.275, 0.276, 0.277, 0.278, 0.279, 0.28, 0.281, 0.282, 0.283, 0.284, or 0.285 mole % rapamycin or rapamycin analogue. In an exemplary embodiment, the RNP particles comprise about 0.275 mole % rapamycin or rapamycin analogue.

(e) Administration

Nanoparticles comprising rapamycin may be administered to a subject by several different means. For instance, nanoparticles may generally be administered parenteraly, intraperitoneally, intravascularly, or intrapulmonarily in dosage unit formulations containing conventional nontoxic pharmaceutically acceptable carriers, adjuvants, and vehicles as desired. The term parenteral as used herein includes subcutaneous, intravenous, intramuscular, intrathecal, or intrasternal injection, or infusion techniques. In one embodiment, the composition may be administered in a bolus. In a preferred embodiment, the composition may be administered intravenously. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and nonionic detergents, and polyethylene glycols can be used. Mixtures of solvents and wetting agents such as those discussed above are also useful.

The RNPs may be administered to a subject once, or multiple times. In some preferred embodiments, the RNPs may be administered once. In other preferred embodiments, the RNPs may be administered multiple times. When administered multiple times, the RNPs may be administered at regular intervals or at intervals that may vary during the treatment of a subject. In some embodiments, the RNPs may be administered multiple times at intervals that may vary during the treatment of a subject. In preferred embodiments, the RNPs may be administered multiple times at regular intervals. In some alternatives of the preferred embodiments, the RNPs may be administered at intervals of about 1, 2, 3, 4, 5, 6, 7, 8, 9, 10, 11, 12, 13, 14, or more days. In other alternatives of the preferred embodiments, the RNPs may be administered at intervals of about 1, 2, 3, 4, 5, 6, 7, 8 or more weeks. In yet other alternatives of the preferred embodiments, the RNPs may be administered at intervals of about 1, 2, 3 or more months. In preferred embodiments, the RNPs may be administered twice weekly.

One of skill in the art will recognize that the amount and concentration of the composition administered to a subject will depend in part on the subject and the reason for the administration (i.e. imaging, drug delivery, etc.). Methods for determining optimal amounts are known in the art. In some embodiments, the RNPs may be administered to the subject in an amount of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2 mL per kilogram of the subject. In other embodiments, the RNPs may be administered to the subject in an amount of about 0.5, 1, 1.5, 2, 2.5, 3, 3.5, 4, 4.5 mL or more per kilogram of the subject.

EXAMPLES

The following examples are included to demonstrate preferred embodiments of the invention.

Introduction for Examples 1-4

Duchenne muscular dystrophy (DMD) is an X-linked progressive muscle degenerative disorder that affects 1:3500 males and is caused by mutations in the dystrophin gene leading to complete absence of dystrophin protein [1]. In contractile tissues, dystrophin is known to play a role in anchoring the cytoskeleton of a muscle cell to the basal lamina. Without proper attachments, coordinated contraction cannot be achieved, explaining in part the weakness observed in these boys. Progressive deterioration of function results from repeated cellular injury as sarcolemmal membranes are susceptible to tearing and disruption as patients age. Primary defects in calcium kinetics have been ascribed to alterations in calcium channel regulatory proteins that contribute to progressive muscle fatigue and failure. Indeed, muscle biopsy specimens from DMD patients have demonstrated an increase in calcium within the muscle cells that can induce apoptosis [2, 3].

Additionally, a strong inflammatory response occurs in the muscle compartment that reflects the age of the process [2]. This immune response is postulated to be a response to cellular necrosis that is amplified based on the large number of cells that are constantly being destroyed and regenerated. The amplified immune infiltration has become the target of therapy with some success. Currently, the only validated therapies for these patients are corticosteroids, which improve strength and overall survival by a combination of membrane stabilization and anti-inflammatory actions [4-7]. Alternative experimental therapies include genetic manipulation to partially restore dystrophin [8], beta blockers [9], and antifibrotic agents [10].

Although a number of animal models of muscular dystrophy exist, the mdx mouse is used extensively for validating proposed therapeutic interventions. The progression of disease and muscle pathology is similar in this animal to human disease, despite being somewhat mild in phenotype [11]. The mdx mouse exhibits three phases of disease, each hallmarked by different microscopic findings. From the time of weaning to 10 weeks of age, the strength in mdx mice improves as they are rapidly growing. From three weeks to 7 weeks, there is an increase in muscle necrosis, thus rendering this period nonideal for drug interventions that rely on strength measurement outcomes. From 10 weeks to 24 weeks, a period of rapid decline in body weight-normalized strength ensues as the muscles simultaneously become weaker and the mouse gains weight. The mouse maintains a basal level of muscle degeneration and regeneration throughout this period [12]. Beyond 24 weeks, mice experience a progressive decline in strength [13].

Recent provocative reports of the use of rapamycin to restore muscle phenotype in dystrophic mice have emerged providing another testable approach to ameliorate the inexorable disease process [14, 15]. Rapamycin is an immunesuppressing macrolide used to prevent organ transplant rejection and as an anti-inflammatory agent to prevent angioplasty restenosis [16-18]. By binding to the mammalian target of rapamycin complex 1 (mTORC1), rapamycin blocks proproliferative, anti-apoptotic signaling [19]. mTORC1 serves as a central node in metabolically active cells with high turnover rates and phosphorylates p70 S6K and 4E-BP1 to promote protein translation by increasing ribosomal synthesis and cap-dependent translation machinery, leading to cell growth. Paradoxically, blocking mTORC1 with rapamycin might be expected to exert deleterious effect on protein synthesis, muscle fiber regeneration, and cell growth in mdx mice. However, rapamycin has also been shown to induce autophagy, a cell survival mechanism that enables the cell to recycle amino acids via the non-specific degradation of long-lived proteins and dysfunctional organelles [20] and may represent a novel mechanism for its unexpected action.

Materials and Methods for Examples 1-4

All chemicals were purchased from Sigma-Aldrich, Inc. (St. Louis, Mo.) unless otherwise specified.

Nanoparticle Formulation

The nanoparticle emulsions were prepared in the following manner. A surfactant co-mixture (600 mg) was prepared by combining 98 mole % purified egg phosphatidylcholine (Avanti Polar Lipids, #840051P) and 2 mole % DPPE (Avanti Polar Lipids, #850705P) and (for the drug containing emulsion only) 0.275 mole % of rapamycin, dissolving the mixture in 3:1 chloroform/methanol, and removing the solvent in vacuo at 40° C. To the dried lipid mixture, 23.4 ml of deionized water containing 2.5% (v/v) of glycerol was added and the lipid reconstituted using an ultrasonic probe. To this reconstituted lipid, 6 ml of perfluorooctyl bromide (PFOB, Exfluor Research Corp.) was added and a coarse emulsion was formed using the ultrasonic probe. This coarse emulsion was transferred to a microfluidizer (M-110S, Microfluidics Corp.) and processed for 4 minutes at a pressure of approximately 17,000 PSI. The resulting emulsion was transferred to a 30 ml serum vial under argon and stored at 4° C.

Animal Studies

Male mdx mice (strain C57BL/10ScSn-Dmdmdx/J) and age-matched controls (strain C57BL/10SnJ) were purchased from The Jackson Laboratory (Bar Harbor, Me.). Starting at age 14 weeks, the mice were injected twice weekly for four weeks with either plain nanoparticles (no drug, n=18 for mdx, n=4 for control) or nanoparticles loaded with 0.275% rapamycin (n=16 for mdx, n=5 for wild-type). Dosage was 1 mL emulsion per kg body weight, delivered through the tail vein. The same treatment regimen was repeated on a subset of each group of mice at age 34 weeks in order to assess age-related changes in strength and treatment effectiveness. Cohort size for each age group was n=7 for mdx/no drug, n=8 for mdx/rapamycin, n=4 for control/no drug, and n=5 for control/rapamycin. No animals in any group demonstrated any apparent adverse effects from the treatment at either 14-18 week ("young") or 34-38 week ("aged") time points.

Treatment effectiveness was determined by measuring forelimb grip strength within one week before beginning each treatment regimen, and subsequently within one week after treatment completion. Strength testing was performed in blinded fashion by an experienced technician using a grip meter attached to a force transducer (E-DF 002 Digital Force Gauge, Chatillon Force Measurement Systems, Largo, Fla.). The tests relied on the animal's instinct to grab hold as it was pulled backward. Each mouse was grasped by the tail and encouraged to grab a trapeze bar attached to the force transducer using its forelimbs. The mouse was then pulled away and the peak force was recorded on a digital display. This procedure was repeated five times sequentially for each animal. The three highest readings were averaged and normalized by the animal's weight to give the strength score.

A separate study was conducted in which rapamycin was administered to mdx and wild-type mice orally. Mice aged 14 weeks were given oral doses of a rapamycin solution (0.067 mg rapamycin/kg body weight) twice per week for a four-week period, mimicking the previous nanoparticle IV injection protocol. The dose volume was set at this level in order to yield an equivalent full body dose to the animals in the nanoparticle injection studies, assuming oral bioavailability to be approximately 10%. Rapamycin powder was solubilized in 190-proof ethanol at 1 mg/mL. This mixture was then diluted 50% in a 1:1 mixture of dextrose and water. A placebo was also formulated that omitted the rapamycin. The treatment solution was administered with a micropipette, typically 40-50 μL per mouse. Forelimb grip strength was measured before and after the full treatment regimen. There were three treatment groups: mdx mice given rapamycin (n=6); control mice given rapamycin (n=6); and mdx mice given placebo (n=6).

Tissue Homogenization

Muscle tissue were extracted from the mdx mice and homogenized in 0.5 mL of RIPA buffer with 1 mM PMSF, Complete Protease Inhibitor Cocktail (Roche, Indianapolis, Ind.), and Phosphatase Inhibitor Cocktail (Roche) using a glass grinding tube. The tissue homogenates were centrifuged at 10,000×g for 10 min at 4° C. and the supernatant was stored at −80° C.

Western Blot Analysis

Proteins in tissue homogenates were resolved on a NuPAGE Novex 4-12% Bis-Tris Gel (Invitrogen NP0336BOX, Carlsbad, Calif.) and transferred to 0.2 μM nitrocellulose membranes (Invitrogen LC2000). Membranes were blocked in 5.0% milk in TBS (G Biosciences R029, St. Louis, Mo.) with 0.05% Tween-20 and incubated with the following primary antibodies: rabbit anti-pS6 (1:1000, Cell Signaling Technology 4857, Boston, Mass.), rabbit anti-S6 (1:1000, Cell Signaling Technology 2217), rabbit anti-LC3B (1:2000, Sigma, St. Louis, Mo.), rabbit anti-Beclin1 (1:1000, Cell Signaling Technology), goat anti-actin (Santa Cruz Biotech). Corresponding secondary antibodies were used at 1:5000. Protein bands were visualized using either ECL Western Blotting Substrate (Pierce 32106, Rockford, Ill.) or Super Signal West Femto Maximum Sensitivity Substrate (Pierce 34095, Rockford, Ill.). Western blot image was used to calculate relative protein expression using densitometry with the open source image analyais package ImageJ (W. S. Rasband, NIH, Bethesda, Md., http://imagej.nih.gov/ij, 1997-2011). Values were normalized to protein bands on ponceau stained membranes (muscle lysates) or actin (cell lysates) and reported as fold change compared to the control, non-treated sample.

Cell Culture

C2C12 cells were obtained from ATCC (Manassas, Va.) and maintained in DMEM supplemented with fetal bovine serum in a 37° C. incubator with 5% $CO_2$. Cells were differentiated by culturing in DMEM+2% horse serum for >4 days. Prior to differentiation, cells were visually checked for confluency. For autophagy flux assays, cells were treated with varied concentrations of nanoparticles, nanoparticles loaded with rapamycin, and equivalent doses of rapamycin dissolved in DMSO. To block flux, bafilomycinA dissolved in DMSO was added to cell culture media. Cells were harvested in RIPA buffer (10 mM Tris-HCL (pH 7.5), 150 mM NaCl, 1.0% IgepalCA-630, 0.5% sodium deoxycholate, 0.1% sodium dodecyl sulfate, 1 mM EDTA, 5% glycerol) with 1 mM PMSF, Complete Protease Inhibitor Cocktail (Roche, Indianapolis, Ind.), and Phosphatase Inhibitor Cocktail (Roche). Cell lysates were collected by saving the supernatant after centrifuging the sample at 10,000×g for 10 min at 4° C. Western blotting was done for LC3 as described above.

Statistics

Statistics were done in collaboration with Dr. William Shannon and colleagues in the Department of Medicine Biostatistics Core using SAS software (SAS Institute, Cary, N.C.).

Example 1

Rapamycin-loaded Nanoparticles Improve Strength in Mdx Animals

An oral and a nanoparticle-based formulation of rapamycin were compared for ability to improve a clinically significant performance factor, muscle grip strength. 14-week old mdx and wild-type mice were treated with eight doses of intravenous nanoparticles over four weeks and standardized grip strength measurements were obtained on each animal before and after therapy. FIG. 1 shows that grip strength increased significantly when rapamycin-loaded nanoparticles (RNP) were employed as therapy (30% increase in strength). Unexpectedly, when NP alone were employed as therapy, grip strength also increased modestly (FIG. 1A) by 8%. When compared to published data collected in the same way used here, this is a remarkable increase in strength as untreated mdx animals typically show a 14.6%+/−5.1% decrease in strength [13]. To determine whether the increase in strength achieved with rapamycin-loaded nanoparticles was due to the drug alone, animals were treated with oral rapamycin administered at 10× the dose provided in the intravenous nanoparticle formulation to account for an expected 10% oral absorption rate [24-27]. Age-matched wild-type mice exhibited no significant increase in strength when treated with rapamycin-loaded nanoparticles or oral rapamycin (FIG. 1B). However, during this age range, wild-type animals typically demonstrate a decrease in strength per weight (−6.6%+/−6.4%), so the increase seen in wild-type animals treated with nanoparticles is interesting.

The cumulative dose of rapamycin given to the animals in the rapamycin-loaded nanoparticle treatment group was within the limits of recommended oral individual dose for patients receiving immunosuppressive therapy when accounting for 18% oral absorption in humans. Further, the intravenous dose used here was approximately 7-fold less than the calculated absorbed oral dose administered to mdx mice by Eghtesad and colleagues to improve muscle pathology [14]. These data indicate that at clinically relevant dose of oral rapamycin for mdx animals, and one that scales up to 4-fold greater than the recommended oral dose for patients, no improvement in strength was obtained. In sharp contrast, the standard dose of rapamycin administered in NP formulations provided marked improvement in grip strength after only 8 i.v. doses. Thus, oral dosing of rapamycin will not affect strength in this model, whereas nanoparticle dosing delivering conventional drug doses appears effective.

To determine whether the increase in strength was both repeatable and independent of the age at which the animals were treated, a subset of treated young animals were given a drug holiday from weeks 18-34, then the nanoparticle dosing was repeated. FIG. 1C shows that over this drug holiday interval, strength declined as anticipated; but that after the repeat dosing of i.v. RNP, strength recovered in the older mdx animals (p=0.008, linear contrast model). The drug holiday data indicate strength declines when off of the drug but that the treatment is reproducible when re-administered and effective over a diverse time interval even late in the disease time course. The observation of strength increase was therefore independent of age, confirming the efficacy of RNP in both younger and older subjects. No significant trend was observed in wild-type mice (FIG. 1D).

Example 2

Systemically Delivered Nanoparticles are Delivered to Mdx Muscles

Figure 2:
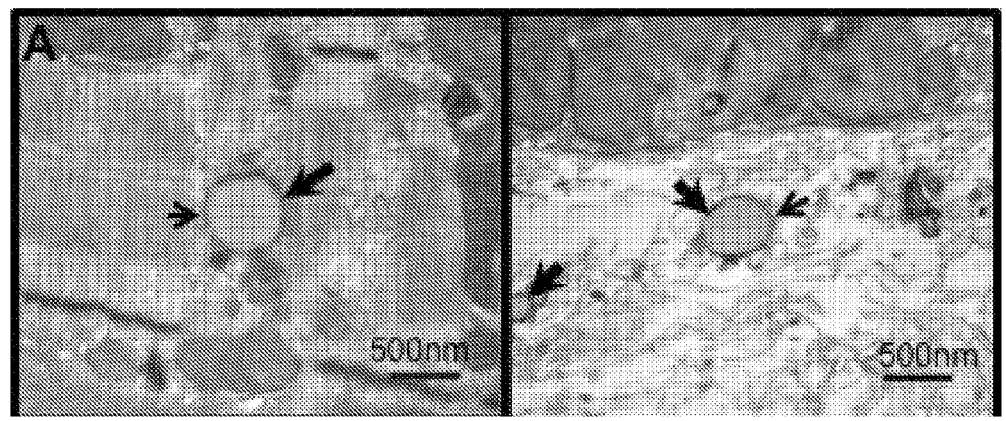
FIG. 2 depicts micrograph images, images of Western blots, and a graph showing that intravenously injected nanoparticles reach the muscles in mdx animals. (A) Nanoparticles (thick arrows) are found both inside mdx mouse muscle (left panel) and in the extracellular matrix of mdx mouse muscle (right panel). Nanoparticles can be distinguished from lipid droplets by the presence of a dark ring surrounding the circle (thin arrow). (B) $^{19}F$ spectroscopy was done on excised muscles to determine the levels of PFOB in mdx muscle. Each of the muscles surveyed showed nanoparticle (PFOB) uptake 24 hrs after last systemic injection. There was no difference in uptake between nanoparticles and rapamycin-loaded nanoparticles in any of the muscles tested (two-tailed t-test). (C) Rapamycin-loaded nanoparticles (R-NP) cause a decrease in S6 levels in mdx animals when compared to nanoparticle (NP) treatment, indicating that the drug rapamycin reaches the muscle tissue and exerts biological activity at the cellular level. However, compared to saline treatment, the nanoparticles increased S6 phosphorylation in all four muscle groups tested, indicating potentially divergent mechanisms of action of the components that could synergize to augment strength, which is a highly novel and unexpected feature of this system. Ponceau stain of blots was done to confirm equivalent protein loading. This same trend is not seen in the muscles from wild-type (WT) animals. (D) Immunohistochemical staining of mdx diaphragm shows variations in pS6 levels between muscle bundles in animals treated with nanoparticles (NP) or rapamycin-loaded nanoparticles (RNP).
Figure 2:
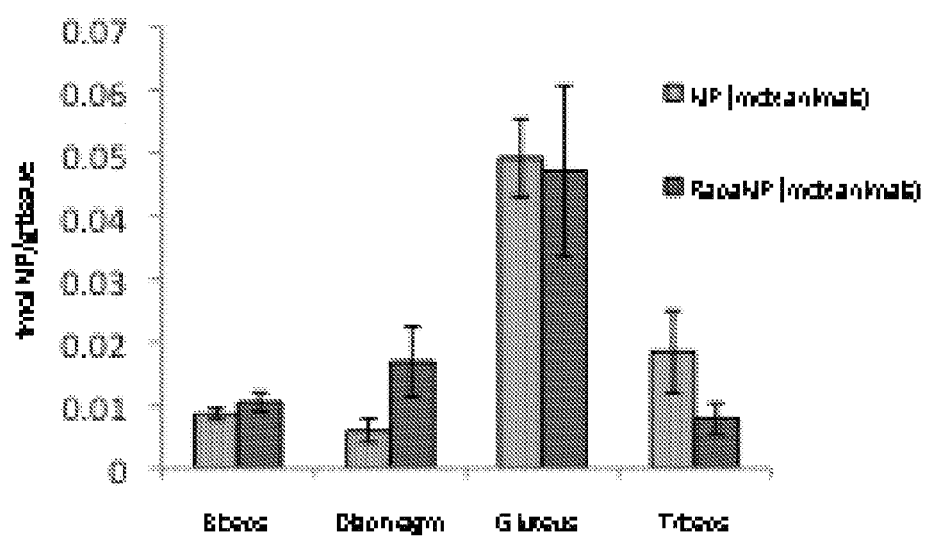
Figure 2:
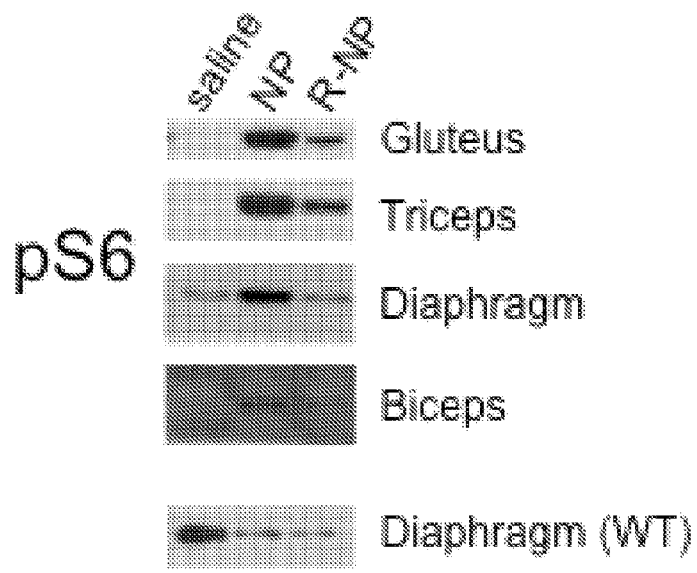
Figure 2:
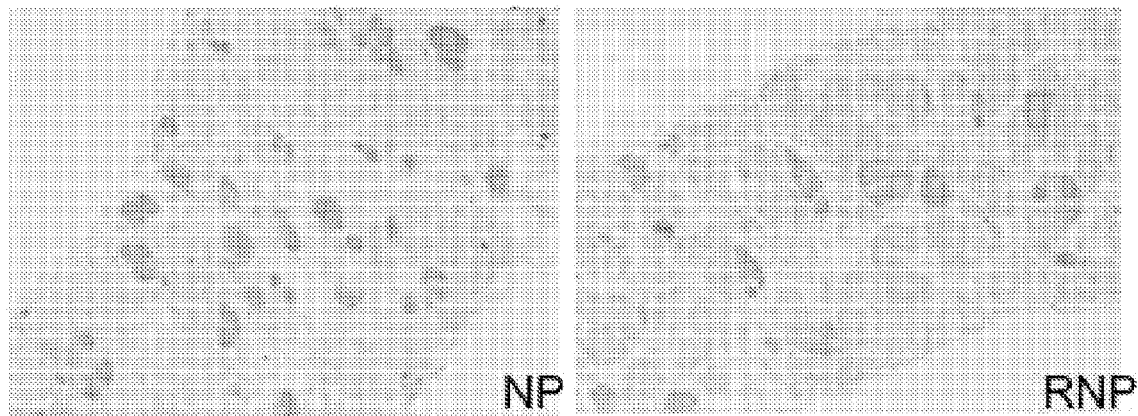

To prove that the nanoparticles themselves are delivered to muscle tissue, transmission electron microscopy (TEM) and fluorine spectroscopy were performed on excised mouse muscles. Fourteen week-old mdx mice and age-matched wild-type mice were treated by lateral tail vein injection for four consecutive days with 1 ml/kg RNP, NP, or saline. Muscles from mdx animals exhibited nanoparticles entrained in and around the muscle cells (FIG. 2A). The particles are distinguishable from disease-induced lipid droplet accumulation by the presence of a dark halo around the nanoparticles. Fluorine spectroscopy to register the $^{19}$F PFOB core of the NP was performed to quantify the concentration of NP in muscle tissue (FIG. 2B). Concentrations of nanoparticles in muscle tissues were calculated by using a standard curve for $^{19}$F spectroscopy. Because baseline levels of $^{19}$F in tissues are negligible, it can be concluded that the spectroscopy signal is solely due to the presence of particles in the muscle. Two-tailed t-tests showed no difference between particle uptake when rapamycin was incorporated into the particles for all muscles tested.

Example 3

Rapamycin Nanoparticles Decrease pS6 Levels

To demonstrate that the drug is acting on the appropriate target once it reaches the muscle, lysates from the muscle were probed from the short time course experiment above for phosphorylated S6. S6 is downstream of mTORC1, so that blocking mTORC1 with rapamycin should cause a decrease in pS6 levels. Indeed, in diaphragm, triceps, biceps, and gluteus, S6 levels were decreased in the mdx animal treated with rapamycin-loaded nanoparticles when compared to mice treated with nanoparticles alone (FIG. 2C). Interestingly, the nanoparticles cause an increase in pS6 levels when compared to saline treated animals. Therefore, the particle is inducing signaling through mTORC1. Adding rapamycin to the particle decreases the amount of signaling, but does not cause it to return to baseline levels. In addition to decreasing the levels of phosphorylation of S6, RNP treatment results in attenuated and more diffuse staining in the mouse diaphragm when compared to the strong, tight staining seen in animals treated with nanoparticles alone (FIG. 2D).

Example 4

Nanoparticle Treatment Restores Autophagy

Figure 3:
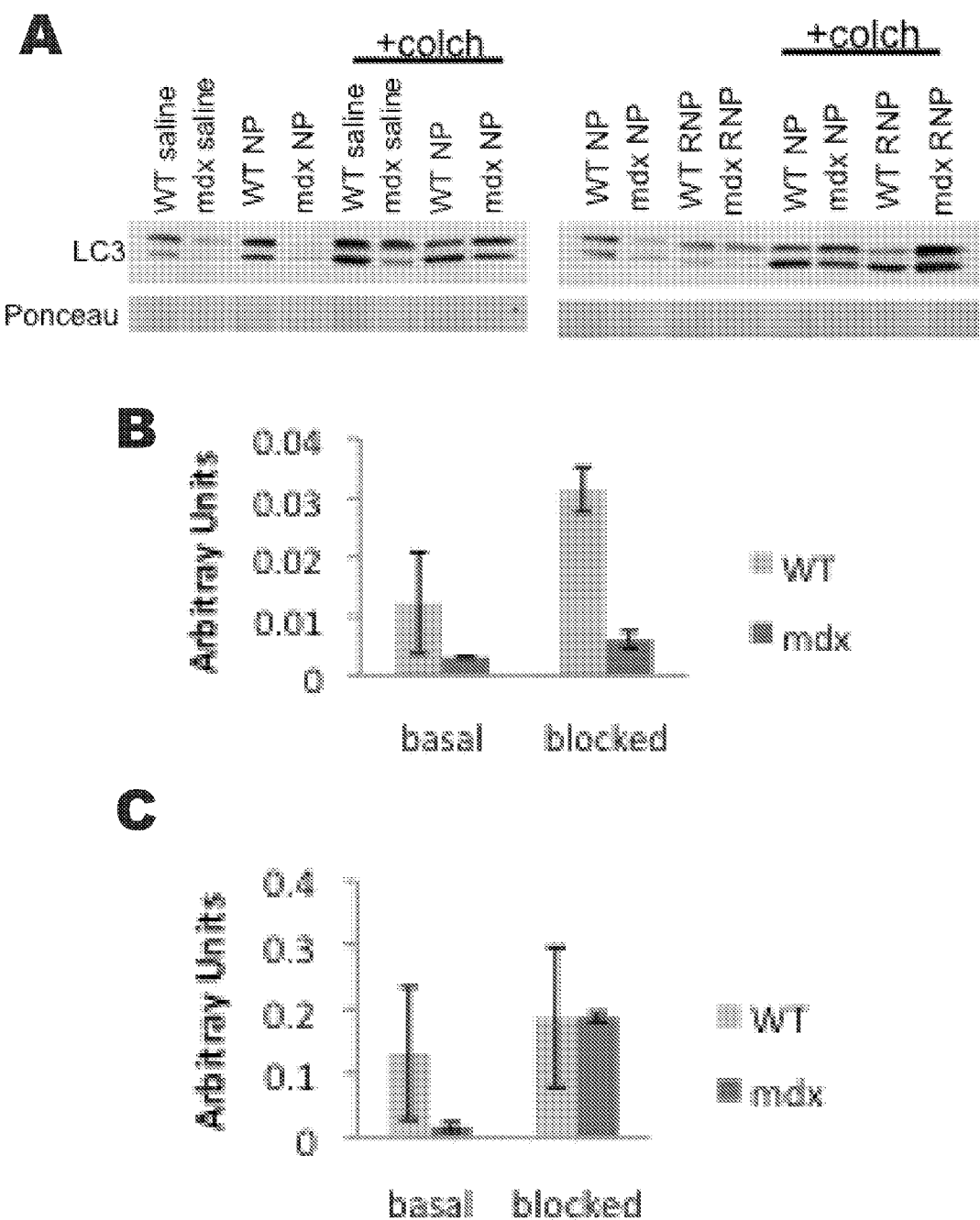
FIG. 3 depicts images of Western blots, and graphs showing that nanoparticles induce autophagy in the diaphragm of mdx animals. (A-D) Representative Western blots demonstrate that both nanoparticle (NP) and rapamycin-loaded nanoparticles (RNP) increase the levels of LC3B-II in the mdx animal, whereas saline treated animals exhibit a low level of LC3B-II expression, even when blocked with colchicine. Wild-type, light grey bars. mdx, dark grey bars. (E) Both Beclin-1 and BNIP3 expression are lower in mdx animals when compared to age-matched wild-type controls. (F) LC3-II levels in differentiated C2C12 cells after treatment with nanoparticles (NP) or rapamycin-loaded nanoparticles (RapaNP) under basal or blocked (bafilomycin-A) conditions. Both NP and RapaNP treatments cause an increase in autophagy flux.
Figure 3:
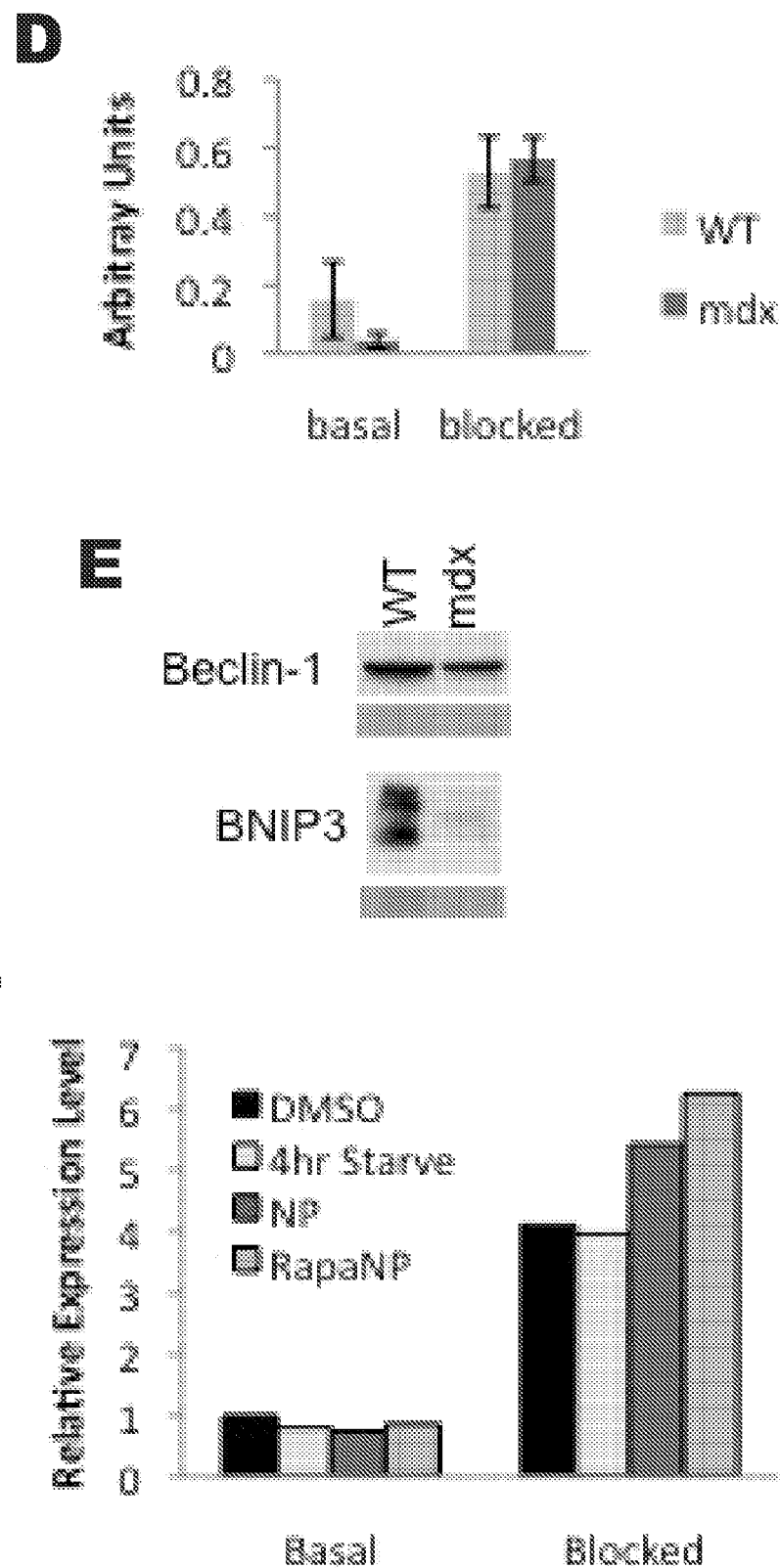

To examine a potential mechanism by which rapamycin-nanoparticles are improving strength in mdx animals, another cohort of the short term treated animals received i.p. injections of colchicine to enable measurement of autophagic flux as previously reported [28]. In the diaphragm, autophagy levels were restored to normal with both nanoparticle and rapamycin-loaded nanoparticle treatment as measured by LC3B-II accumulation even when blocked with colchicine, indicative of a previously unreported defect in autophagy in the mdx mouse (FIG. 3A-D). The apparent defect in autophagy in mdx mice is also demonstrated by a reduction in Beclin-1 and BNIP3 expression in the diaphragm when compared to an age-matched control animal (FIG. 3E).

To validate the induction of autophagy in muscle cells by nanoparticles, C2C12 cells were allowed to grow to confluence and then differentiated into myotubes. These myotubes were subjected to treatment with nanoparticles. To assess autophagy flux, additional samples were treated with bafilomycin to block autophagy progression. LC3B levels were higher in cells treated with nanoparticles of rapamycin-loaded nanoparticles, thereby suggesting an induction of autophagy, and indicating that basally suppressed autophagy can be rescued by this therapeutic strategy (FIG. 3F).

Discussion for Examples 1-4

It has been shown for the first time that rapamycin-loaded nanoparticles improve strength in a mouse model of Duchenne muscular dystrophy and that the observed improvement may be due to restoring a disease-related defect in autophagy. Previous work has demonstrated improvement in muscle pathology when mdx animals were treated with oral rapamycin or a microparticle intramuscular (i.m.) depot injection of rapamycin [14]. In that study, immune infiltration was decreased and muscles were healthier as judged by increased proliferative capacity and decreased necrosis. However, no physiological metrics were presented to conclude that this approach would be efficacious as a clinical strategy. Here, an increase in strength was demonstrated after systemic treatment with rapamycin-loaded nanoparticles that is both repeatable and capable of enhancing performance in both younger and older subjects. Interestingly, this approach achieves the strength increase with systemic rapamycin dosing at a quarter of the initial rapamycin depot injection reported by Eghtesad et al. [14].

It has also been demonstrated that the nanoparticle formulation of rapamycin is key to achieving this strength increase, as rapamycin given orally at pharmacological doses to compensate for decreased oral bioavailability does not improve strength in mdx animals. The potential clinical utility for nanoparticle-based drug delivery derives from the concept of decreasing systemic dosing while increasing local delivery by molecular targeting of the particles to specific cell types [29, 30]. Additionally, the incorporation of traditional chemotherapeutics into nano- and microcarriers has increased their circulation time and therefore increased therapeutic effect simply by having the drug cleared more slowly while being retained in particle that theoretically exerts less effect on normal than on pathological tissues [31].

Interestingly, it could be that the nanoparticle carrier itself may have some strength promoting capacity. Whether this is due to the addition of lipids to the cell thereby stabilizing the dysfunctional muscle cell membrane, the initiation of undescribed cell signaling events, or other factors is unclear. Regardless, the strong enhancement of S6 phosphorylation seen in the mdx animals after nanoparticle treatment suggests that the particles do drive the mTORC1 cell signaling pathway. Previously it has been shown that protein synthesis is shut off in the high intracellular calcium environment found in muscles of muscular dystrophy patients and mouse models [32, 33]. Possibly some of the benefit of the nanoparticle drug delivery is due to reinstatement of protein synthesis via promotion of mTORC1 signaling.

The enhancement of S6 phosphorylation is particularly interesting given that the diaphragm of mdx mice is reported to be unable to increase mTOR activity with age [34]. Considering that respiratory and cardiac failure are the major causes of death in patients with DMD, the underlying molecular cause of this failure may be due to a lack of capacity to regenerate muscle fibers, especially in cardiac and diaphragm muscle cells as these are in constant use throughout life and therefore most likely to exhaust regenerative capacity sooner than other muscles. The addition of rapamycin to the particle decreased the level of pS6, but did not reduce it to baseline, suggesting that some signal promotion was still occurring in these cells, which may be one factor contributing to an increase in strength.

Skeletal muscle, including the diaphragm, comprises different fiber types, each of which prefer different methods of energy derivation. Fibers that utilize oxidative phosphorylation are thought to better resist fatigue as compared to the fast twitch fibers that use glycolysis [35]. Interestingly, mTOR also plays a role in metabolism as it has been shown to transcriptionally activate mitochondrial genes related to oxidative phosphorylation [36]. Further, completely blocking mTORC1 in the muscle via knocking out raptor [37] or knocking out mTOR [38] causes a decrease in oxidative capacity and increase in glucose and glycogen uptake, respectively. Therefore, it may be the case that the mTORC1 activation observed by an increase in S6 phosphorylation in animals treated with nanoparticles may be promoting oxidative phosphorylation in these muscles and thereby enhancing the capacity of fatigue-resistant muscle fibers. Unlike the studies using genetic manipulation, our use of rapamycin did not completely block the mTORC1 signal and may therefore be permissive of this phenomenon.

Rapamycin also exhibits mTORC1 independent effects when it binds to FKBP12 on the ryanodine receptor. Previous studies suggest that binding of rapamycin disrupts the ryanodine receptor's functions and therefore would be expected to elicit dysfunctional calcium handling [39, 40]. However, in mdx animals, the ryanodine receptor itself appears to be dysfunctional [41]. Perhaps it is the case that the addition of rapamycin acts to block some of these receptors and help modulate a more normal calcium handling or acts to decrease the expression of the receptors as has been previously reported [42].

The work presented here demonstrates restoration of autophagy in the muscles of mdx animals when they are treated with rapamycin-loaded nanoparticles and in C2C12 myotubes in culture. Autophagy is a bulk degradation pathway that is used to recycle amino acids and other cellular building blocks. Originally demonstrated to be a normal response to nutrient stress, dysfunctional autophagy is now understood to play a role in a broad range of diseases including various cancers, diabetes, heart disease, and neurodegenerative disorders [43, 44]. In the field of neuromuscular disorders, inclusion-body myopathy has been shown to be caused by mutations in a protein necessary for proper autophagy [45]. Defects in autophagy also play a role in Pompe disease[46].

More recently, defects in autophagy has been reported in collagen-6 knock-out mice, a mouse model of Bethlem myopathy and Ullrich congenital muscular dystrophy [15]. Genetic, dietary, and pharmaceutical approaches, including rapamycin, for inducing autophagy in the Col6a−/− mice all resulted in improvement in the dystrophic phenotype. Here, we illustrate increased autophagy in mdx mouse muscles after rapamycin-nanoparticle treatment. While it has been proposed that induction of autophagy by rapamycin is cell-type specific with muscle cells being insensitive to rapamycin [47, 48], in sharp contrast we find that when administered on a nanoparticle, rapamycin is capable of inducing autophagy in the muscles of mdx animals. The ability to repeat this observation after a drug holiday in aging subjects is conclusive for the effect.

This latter effect is most exciting and clinically relevant, as the increase in strength after treatment is not restricted to the early to mid stage of the disease in the mouse model, but can also improve strength much later in the course of the disease. This observation is hopeful as previous studies have demonstrated improvement in strength in the mdx animal very early in the disease course, but have not proven beneficial as the disease progresses [13]. Further to clinical translation, it was demonstrated the efficacy of rapamycin-loaded nanoparticles at drug doses lower than would be administered orally to patients. Unfortunately, there is no apparent benefit to strength when the plain drug is given orally, even at pharmacological doses. Additionally, it would be expected that patients might prefer i.v injections rather than multi-site microparticle intramuscular depot injections as previously reported to improve muscle pathology [14]. Because rapamycin is an approved agent for other diseases, and because these perfluorocarbon nanoparticles have demonstrated an excellent safety record in clinical trials as a blood substitute at far greater doses than used in this study [49-51], or in other experimental studies when used for targeted molecular imaging and therapeutics [52-55], the rapamycin nanoparticle construct could represent a promising candidate for trials in muscular dystrophy.

References for Examples 1-4

1. Hoffman, E. P., R. H. Brown, Jr., and L. M. Kunkel, Dystrophin: the protein product of the Duchenne muscular dystrophy locus. Cell, 1987. 51(6): p. 919-28.
2. Bodensteiner, J. B. and A. G. Engel, Intracellular calcium accumulation in Duchenne dystrophy and other myopathies: a study of 567,000 muscle fibers in 114 biopsies. Neurology, 1978. 28(5): p. 439-46.
3. Zeman, R. J., et al., Regulation of protein degradation in muscle by calcium. Evidence for enhanced nonlysosomal proteolysis associated with elevated cytosolic calcium. J Biol Chem, 1985. 260(25): p. 13619-24.
4. Moxley, R. T., 3rd, et al., Practice parameter: corticosteroid treatment of Duchenne dystrophy: report of the Quality Standards Subcommittee of the American Academy of Neurology and the Practice Committee of the Child Neurology Society. Neurology, 2005. 64(1): p. 13-20.
5. Markham, L. W., et al., Steroid therapy and cardiac function in Duchenne muscular dystrophy. Pediatr Cardiol, 2005. 26(6): p. 768-71.
6. Biggar, W. D., et al., Long-term benefits of deflazacort treatment for boys with Duchenne muscular dystrophy in their second decade. Neuromuscul Disord, 2006. 16(4): p. 249-55.
7. Balaban, B., et al., Corticosteroid treatment and functional improvement in Duchenne muscular dystrophy: long-term effect. Am J Phys Med Rehabil, 2005. 84(11): p. 843-50.
8. Nelson, S. F., et al., Emerging genetic therapies to treat Duchenne muscular dystrophy. Curr Opin Neurol, 2009. 22(5): p. 532-8.
9. Ogata, H., Y. Ishikawa, and R. Minami, Beneficial effects of beta-blockers and angiotensin-converting enzyme inhibitors in Duchenne muscular dystrophy. J Cardiol, 2009. 53(1): p. 72-8.

10. Rafael-Fortney, J. A., et al., Early Treatment With Lisinopril and Spironolactone Preserves Cardiac and Skeletal Muscle in Duchenne Muscular Dystrophy Mice. Circulation.
11. Bulfield, G., et al., X chromosome-linked muscular dystrophy (mdx) in the mouse. Proc Natl Acad Sci USA, 1984. 81(4): p. 1189-92.
12. McGeachie, J. K., et al., Age-related changes in replication of myogenic cells in mdx mice: quantitative autoradiographic studies. J Neurol Sci, 1993. 119(2): p. 169-79.
13. Keeling, R. M., et al., Weekly oral prednisolone improves survival and strength in male mdx mice. Muscle Nerve, 2007. 35(1): p. 43-8.
14. Eghtesad, S., et al., Rapamycin ameliorates dystrophic phenotype in mdx mouse skeletal muscle. Mol Med.
15. Grumati, P., et al., Autophagy is defective in collagen VI muscular dystrophies, and its reactivation rescues myofiber degeneration. Nat Med. 16(11): p. 1313-20.
16. Thomson, A. W., H. R. Turnquist, and G. Raimondi, Immunoregulatory functions of mTOR inhibition. Nat Rev Immunol, 2009. 9(5): p. 324-37.
17. Vilquin, J. T., et al., Successful myoblast allotransplantation in mdx mice using rapamycin. Transplantation, 1995. 59(3): p. 422-6.
18. Adelman, S. J., Sirolimus and its analogs and its effects on vascular diseases. Curr Pharm Des. 16(36): p. 4002-11.
19. Wullschleger, S., R. Loewith, and M. N. Hall, TOR signaling in growth and metabolism. Cell, 2006. 124(3): p. 471-84.
20. Shigemitsu, K., et al., Regulation of translational effectors by amino acid and mammalian target of rapamycin signaling pathways. Possible involvement of autophagy in cultured hepatoma cells. J Biol Chem, 1999. 274(2): p. 1058-65.
21. Greish, K., Enhanced permeability and retention of macromolecular drugs in solid tumors: a royal gate for targeted anticancer nanomedicines. J Drug Target, 2007. 15(7-8): p. 457-64.
22. Iyer, A. K., et al., Exploiting the enhanced permeability and retention effect for tumor targeting. Drug Discov Today, 2006. 11(17-18): p. 812-8.
23. Maeda, H., G. Y. Bharate, and J. Daruwalla, Polymeric drugs for efficient tumor-targeted drug delivery based on EPR-effect. Eur J Pharm Biopharm, 2009. 71(3): p. 409-19.
24. Napoli, K. L., et al., Distribution of sirolimus in rat tissue. Clin Biochem, 1997. 30(2): p. 135-42.
25. Stepkowski, S. M., Preclinical results of sirolimus treatment in transplant models. Transplant Proc, 2003. 35(3 Suppl): p. 219S-226S.
26. O'Reilly, T., et al., Comparative pharmacokinetics of RAD001 (everolimus) in normal and tumor-bearing rodents. Cancer Chemother Pharmacol. 65(4): p. 625-39.
27. Crowe, A., et al., Absorption and intestinal metabolism of SDZ-RAD and rapamycin in rats. Drug Metab Dispos, 1999. 27(5): p. 627-32.
28. Ju, J. S., et al., Quantitation of "autophagic flux" in mature skeletal muscle. Autophagy. 6(7): p. 929-35.
29. Pan, D., et al., Nanomedicine: perspective and promises with ligand-directed molecular imaging. Eur J Radiol, 2009. 70(2): p. 274-85.
30. Blanco, E., et al., Nanomedicine in cancer therapy: innovative trends and prospects. Cancer Sci. 102(7): p. 1247-52.
31. Samad, A., Y. Sultana, and M. Aqil, Liposomal drug delivery systems: an update review. Curr Drug Deliv, 2007. 4(4): p. 297-305.
32. Williams, D. A., et al., Resting calcium concentrations in isolated skeletal muscle fibres of dystrophic mice. J Physiol, 1990. 428: p. 243-56.
33. Zeman, R. J., et al., Regulation of Ca2+-dependent protein turnover in skeletal muscle by thyroxine. Biochem J, 1986. 240(1): p. 269-72.
34. Mouisel, E., et al., Muscle weakness and atrophy are associated with decreased regenerative capacity and changes in mTOR signaling in skeletal muscles of venerable (18-24-month-old) dystrophic mdx mice. Muscle Nerve. 41(6): p. 809-18.
35. Kilarski, W. and M. Sjostrom, Systematic distribution of muscle fibre types in the rat and rabbit diaphragm: a morphometric and ultrastructural analysis. J Anat, 1990. 168: p. 13-30.
36. Cunningham, J. T., et al., mTOR controls mitochondrial oxidative function through a YY1-PGC-1alpha transcriptional complex. Nature, 2007. 450(7170): p. 736-40.
37. Bentzinger, C. F., et al., Skeletal muscle-specific ablation of raptor, but not of rictor, causes metabolic changes and results in muscle dystrophy. Cell Metab, 2008. 8(5): p. 411-24.
38. Risson, V., et al., Muscle inactivation of mTOR causes metabolic and dystrophin defects leading to severe myopathy. J Cell Biol, 2009. 187(6): p. 859-74.
39. Avila, G., et al., FKBP12 binding to RyR1 modulates excitation-contraction coupling in mouse skeletal myotubes. J Biol Chem, 2003. 278(25): p. 22600-8.
40. Ahern, G. P., P. R. Junankar, and A. F. Dulhunty, Ryanodine receptors from rabbit skeletal muscle are reversibly activated by rapamycin. Neurosci Lett, 1997. 225(2): p. 81-4.
41. Bellinger, A. M., et al., Hypernitrosylated ryanodine receptor calcium release channels are leaky in dystrophic muscle. Nat Med, 2009. 15(3): p. 325-30.
42. Avila, G. and R. T. Dirksen, Rapamycin and FK506 reduce skeletal muscle voltage sensor expression and function. Cell Calcium, 2005. 38(1): p. 35-44.
43. Levine, B. and G. Kroemer, Autophagy in the pathogenesis of disease. Cell, 2008. 132(1): p. 27-42.
44. Gonzalez, C. D., et al., The emerging role of autophagy in the pathophysiology of diabetes mellitus. Autophagy. 7(1): p. 2-11.
45. Ju, J. S., et al., Valosin-containing protein (VCP) is required for autophagy and is disrupted in VCP disease. J Cell Biol, 2009. 187(6): p. 875-88.
46. Raben, N., et al., Suppression of autophagy in skeletal muscle uncovers the accumulation of ubiquitinated proteins and their potential role in muscle damage in Pompe disease. Hum Mol Genet, 2008. 17(24): p. 3897-908.
47. Mammucari, C., et al., FoxO3 controls autophagy in skeletal muscle in vivo. Cell Metab, 2007. 6(6): p. 458-71.
48. Sandri, M., Autophagy in health and disease. 3. Involvement of autophagy in muscle atrophy. Am J Physiol Cell Physiol. 298(6): p. C1291-7.
49. Clark, L. C., Jr., et al., Room temperature-stable biocompatible fluorocarbon emulsions. Prog Clin Biol Res, 1983. 122: p. 169-80.
50. Flaim, S. F., Pharmacokinetics and side effects of perfluorocarbon-based blood substitutes. Artif Cells Blood Substit Immobil Biotechnol, 1994. 22(4): p. 1043-54.
51. Keipert, P. E., et al., Enhanced oxygen delivery by perflubron emulsion during acute hemodilution. Artif Cells Blood Substit Immobil Biotechnol, 1994. 22(4): p. 1161-7.
52. Hu, G., et al., Imaging of Vx-2 rabbit tumors with alpha (nu)beta3-integrin-targeted 111 In nanoparticles. Int J Cancer, 2007. 120(9): p. 1951-7.

53. Cyrus, T., et al., Intramural delivery of rapamycin with alphavbeta3-targeted paramagnetic nanoparticles inhibits stenosis after balloon injury. Arterioscler Thromb Vasc Biol, 2008. 28(5): p. 820-6.
54. Schmieder, A. H., et al., Molecular MR imaging of melanoma angiogenesis with alphanubeta3-targeted paramagnetic nanoparticles. Magn Reson Med, 2005. 53(3): p. 621-7.
55. Winter, P. M., et al., Endothelial alpha(v)beta3 integrin-targeted fumagillin nanoparticles inhibit angiogenesis in atherosclerosis. Arterioscler Thromb Vasc Biol, 2006. 26(9): p. 2103-9.

Example 5

Rapamycin-loaded Nanoparticles Improve Ejection Fraction Strength in Older Mdx Animals The effect of rapamycin-loaded nanoparticles on cardiac muscle strength in mdx and wild type animals was measured. Seven 17 month old mdx mice, and nine 17 month old wild type (WT) mice were separated into rapamycin treated groups (rapamycin-treated mdx mice N=3; rapamycin-treated WT mice N=5) and untreated groups (untreated mdx mice N=4; untreated WT mice N=4). The rapamycin treated groups received eight evenly separated IV injections of rapamycin-loaded nanoparticles in four weeks (0.275 mol % rapamycin in perfluoro-octyl bromide nanoparticle, 1.5 mL/g body weight). All mice were lightly anesthetized with isoflurane for imaging at the age of 18 month. The body temperature was maintained with a heating pad and thermistor-controlled heating lamp. Heated ultrasound coupling gel was applied to the shaved chest area. Parasternal short-axis (SAX) and parasternal long-axis (LAX) views of the left ventricle were acquired using a commercially available ultrasound scanning system (Spark, Ardent Sound, Inc., Mesa, Ariz.) with a high-frequency linear array (16 MHz, 128-element). Waveforms were sampled at 66.67 MHz. Two hundred frames of cardiac data were acquired for each view at a frame rate of 152 Hz, with each frame consisting of 128 A-lines. Each loop thus consisted of between 8 and 12 heart cycles. RF data was analyzed in custom plugins written for ImageJ (Rasband, W. S., ImageJ, U.S. National Institutes of Health, Bethesda, Md.). The resulting image loops were scaled to a resolution of 0.05 mm/pixel. Ejection fraction was computed using ImageJ by manually tracing the ventricular endocardium border at systole and diastole in the SAX view for each beat and recording the area region of interest (ROI). Left ventricular volume at systole (or diastole) was estimated by computing the volume of an ellipsoid having a circular cross-section equal to the mean systolic (or diastolic) ROI area and length equal to the mean systolic (or diastolic) measured ventricular length in LAX. Ejection fraction (EF) was then computed as the ratio of the difference in volume of this ellipsoid between diastole and systole.

Figure 4:
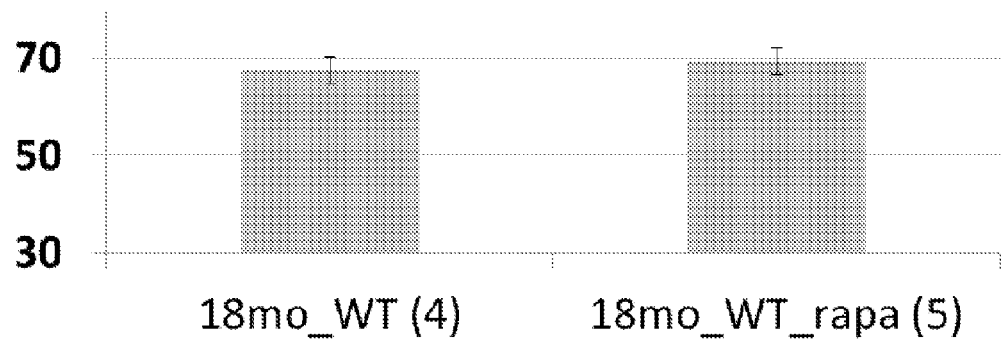
FIG. 4 depicts two plots showing improved cardiac muscle strength in older mdx mice treated with rapamycin-loaded nanoparticles. (A) Plot showing ejection fraction in 18 month old WT mice treated with rapamycin-loaded nanoparticles and in untreated 18 month old WT mice. (B) Plot showing ejection fraction in 18 month old mdx mice treated with rapamycin-loaded nanoparticles and in untreated 18 month old mdx mice.
Figure 4:
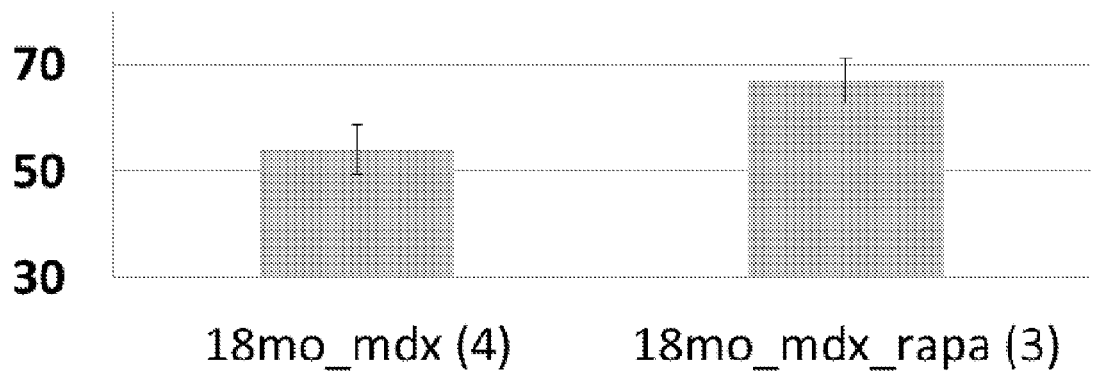

EF was improved in the treated mdx mice (67±4.3%), compared to the untreated mdx mice (54±4.7%) (FIG. 4A). EF in the treated WT mice was not improved (FIG. 4B), consistent with the discovered function of rapamycin-loaded nanoparticles in improving muscle strength of deteriorating muscle tissue, but not muscle strength of normal muscle tissue.

Example 6

Rapamycin-loaded Nanoparticles Improve Pull Strength in Older Wild Type Animals

Figure 5:
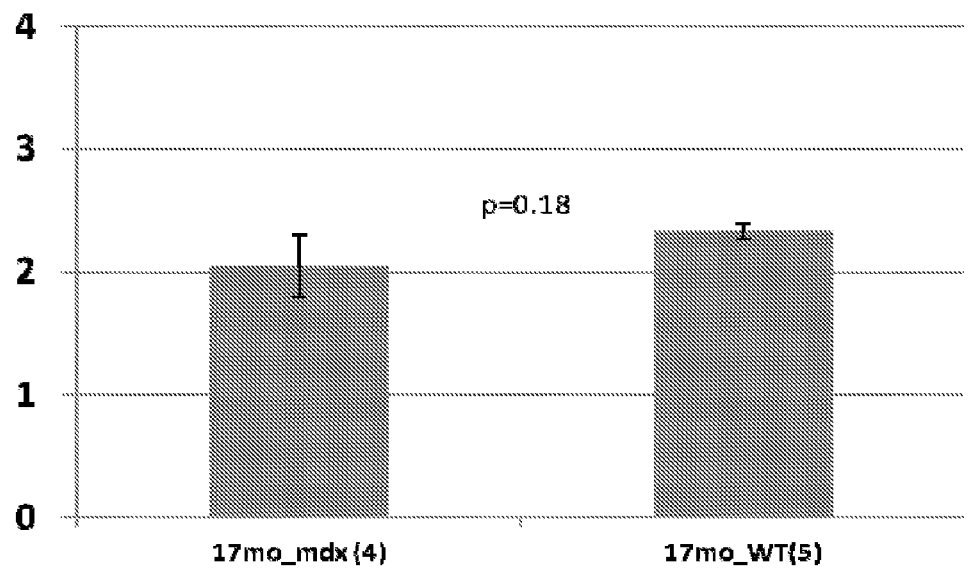
FIG. 5 depicts two plots showing improved pulling strength in older wildtype mice treated with rapamycin-loaded nanoparticles. (A) Plot showing pulling strength per body weight in 17 month old mdx and WT mice before treatment with rapamycin-loaded nanoparticles. (B) Plot showing pulling strength per body weight in 18 month old mdx and wt WT mice after treatment with rapamycin-loaded nanoparticles. (C) Plot showing side by side comparison of pulling strength per body weight in 17 month old WT mice before treatment with rapamycin-loaded nanoparticles from plot in (A) and pulling strength per body weight in 18 month old WT mice after on month treatment with rapamycin-loaded nanoparticles from plot in (B). (D) Plot showing change in pulling strength per body weight in mdx and WT mice after one month treatment with rapamycin-loaded nanoparticles.
Figure 5:
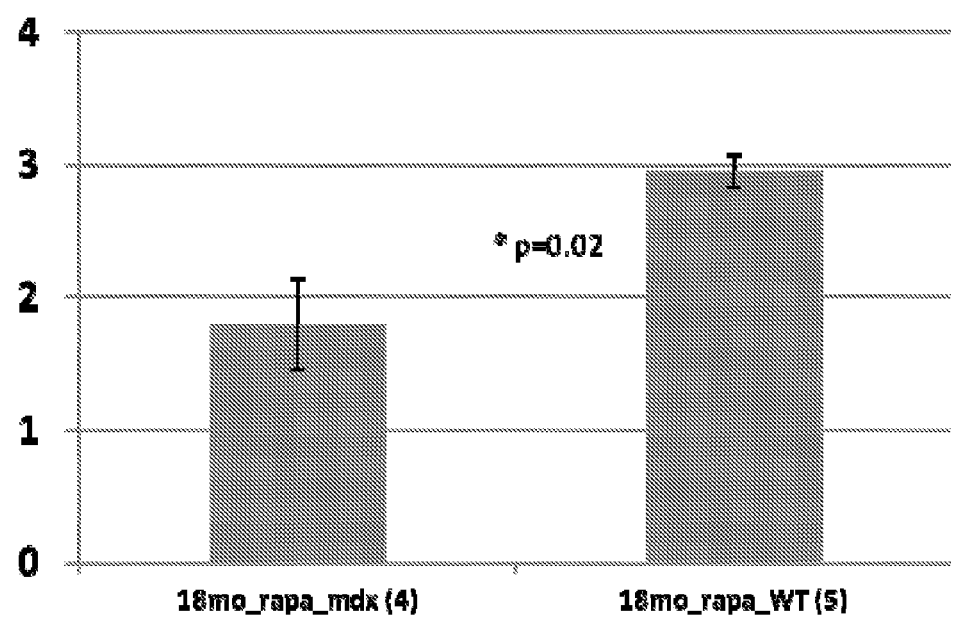
Figure 5:
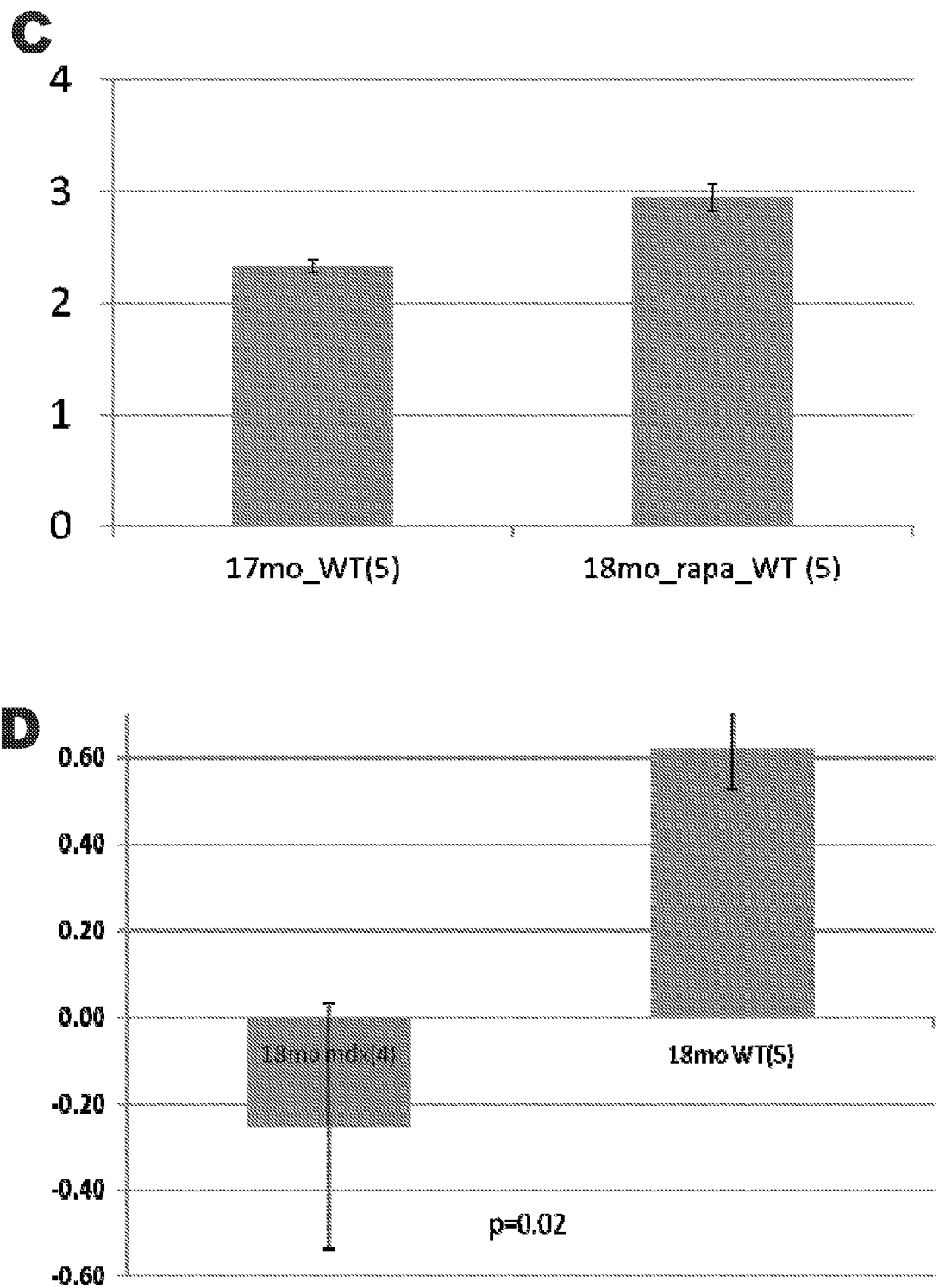

Five 17 month old wildtype mice (BL/10, Jackson Laboratories, Bar Harbor, Me.), and four 17 month old mdx mice were weighted and examined for forelimb strength before (FIG. 5A) and after rapamycin nanoparticle treatment (FIG. 5B). The rapamycin treatment consisted of 0.275 mol % rapamycin in perfluoro-octyl bromide nanoparticle administered at 1.5 mL/g body weight, twice per week, for four weeks. Strength testing consisted of five separate measurements using a trapeze bar attached to a force transducer that recorded peak generated force (Stoelting, Wood-Dale, Ill.). Mice instinctively grab the bar with their forepaws and continue to hold while being pulled backwards by the tail, releasing only when unable to maintain grip. The resulting measurement was recorded and the three highest measurements were averaged to give the strength score.

After treatment, strength(g) per body weight(g) in WT mice was improved by 27% from 2.33±0.06 to 2.95±0.13 (FIG. 5C). Strength in the treated mdx mice was not improved (FIG. 5D), consistent with the anticipated lack of efficacy toward skeletal muscle strength in the end stages of the disease process. Also, as the heart disease in mdx mice and DMD patients is known to develop later in the disease process than does the skeletal myopathy, it is not surprising that efficacy is observed regarding improved heart function in the later stages of the disease.

Example 7

Figure 6:
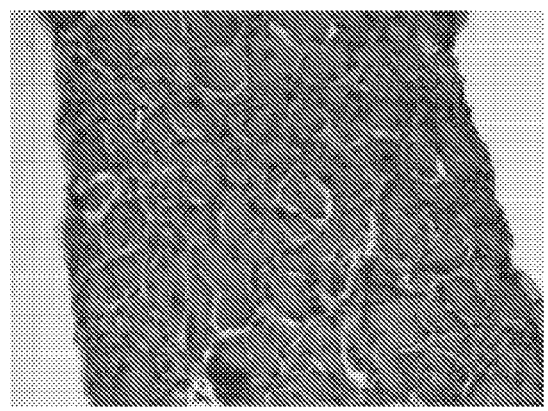
FIG. 6 depicts micrograph images of diaphragm muscle in mdx animals. (A) Diaphragm muscle stained with hematoxylin and eosin. (B) Rhodamine-labeled nanoparticles in the diaphragm muscle. (C) Cy7-labeled rapamycin in the diaphragm muscle.
Figure 6:
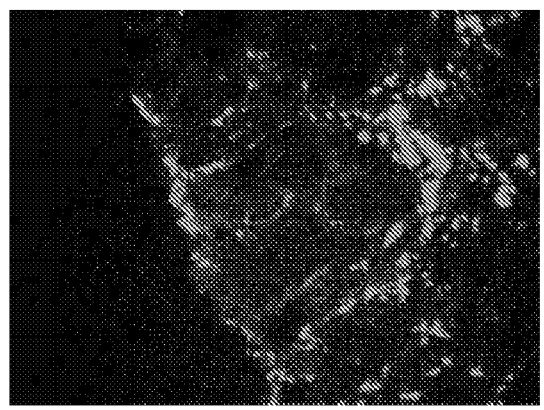
Figure 6:
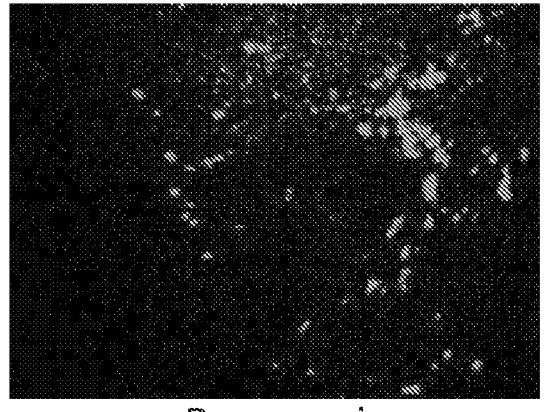

Fluorescence Staining of Nanoparticle and Rapamycin Deposition in the Diaphragm of Mdx Mice A mouse diaphragm muscle was excised from an mdx mouse treated with rapamycin-loaded nanoparticles (FIG. 6A). The nanoparticles were rhodamine-labeled, and the rapamycin was labeled with Cy-7. The diaphragm muscle exhibited deposited nanoparticles entrained in and around the muscle cells (FIG. 6B). Rapamycin showed both punctate and diffuse staining, indicative of diffusion of rapamycin into distant muscle tissues (FIG. 6C).

What is claimed is:

1. A method for increasing muscle strength in a subject, the method comprising administering rapamycin-loaded nanoparticles to a subject in need of increased muscle strength.
2. The method of claim 1, wherein the subject has muscular dystrophy.
3. The method of claim 1, wherein the subject is suffering from muscle weakness resulting from aging.
4. The method of claim 1, wherein the subject is suffering from muscle weakness resulting from a traumatic injury or surgery.
5. The method for claim 1, wherein the administration of rapamycin-loaded nanoparticles induces autophagy of muscle cells.
6. The method for claim 1, wherein the administration of rapamycin-loaded nanoparticles attenuates muscle destruction.
7. The method for claim 1, wherein the rapamycin-loaded nanoparticles are administered intravenously.
8. The method for claim 1, wherein the rapamycin-loaded nanoparticles comprise between about 0.1 and 0.5% rapamycin.
9. The method for claim 1, wherein the rapamycin-loaded nanoparticles are administered at least once a week.
10. The method for claim 1, wherein 1 mL/kg of the rapamycin-loaded nanoparticles are administered at least once a week.

11. A method for attenuating muscle destruction in a subject, the method comprising administering rapamycin-loaded nanoparticles to a subject experiencing muscle destruction.

12. The method for claim 11, wherein the administration of rapamycin-loaded nanoparticles induces autophagy.

13. The method for claim 11, wherein the rapamycin-loaded nanoparticles are administered intravenously.

14. The method for claim 11, wherein the rapamycin-loaded nanoparticles comprise between about 0.1 and 0.5% rapamycin.

15. The method for claim 11, wherein the rapamycin-loaded nanoparticles are administered at least once a week.

16. A method for inducing autophagy in the muscle cells of a subject, the method comprising administering rapamycin-loaded nanoparticles so that autophagy is increased in the muscle cells of the subject.

17. The method for claim 16, wherein the administration of rapamycin-loaded nanoparticles attenuates muscle destruction.

18. The method for claim 16, wherein the rapamycin-loaded nanoparticles are administered intravenously.

19. The method for claim 16, wherein the rapamycin-loaded nanoparticles comprise between about 0.1 and 0.5% rapamycin.

20. The method for claim 16, wherein the rapamycin-loaded nanoparticles are administered at least once a week.

* * * * *